（12）United States Patent
Meyers

(10) Patent No.: US 7,060,476 B2
(45) Date of Patent: Jun. 13, 2006

(54) 27411, A NOVEL HUMAN PGP SYNTHASE

(75) Inventor: Rachel E. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 153 days.

(21) Appl. No.: 10/229,662

(22) Filed: Aug. 28, 2002

(65) Prior Publication Data

US 2003/0040017 A1    Feb. 27, 2003

Related U.S. Application Data

(62) Division of application No. 09/795,691, filed on Feb. 28, 2001, now Pat. No. 6,465,230.

(60) Provisional application No. 60/185,517, filed on Feb. 28, 2000.

(51) Int. Cl.
| | |
|---|---|
| C12N 9/12 | (2006.01) |
| C12N 1/20 | (2006.01) |
| C12Q 1/68 | (2006.01) |
| C12Q 1/48 | (2006.01) |
| C07H 21/04 | (2006.01) |
| A01N 25/00 | (2006.01) |
| C12P 21/04 | (2006.01) |
| C12Q 1/00 | (2006.01) |

(52) U.S. Cl. .............. 435/193; 435/15; 435/4; 435/6; 435/252.3; 435/320.1; 435/69.1; 536/23.2; 536/23.5; 514/789

(58) Field of Classification Search ................ 435/194, 435/252.3, 320.1, 71.1, 4, 6, 7.7, 7.71, 7.9, 435/7.92, 7.93, 325, 193, 15, 69.1; 536/23.2, 536/23.5; 514/789
See application file for complete search history.

(56) References Cited

FOREIGN PATENT DOCUMENTS

WO    WO01/02568    1/2001

OTHER PUBLICATIONS

Chang, S.C., et al., "The PEL1 Gene (Renamed PGS1) Encodes the Phosphatidylglycero-Phosphate Synthase of *Saccharomyces cerevisiae*," *The Journal of Biochemical Chemistry*, Apr. 17, 1998, pp. 9829-9836, vol. 273(16).
Gopalakrishnan, A.S., et al., "Structure and Expression of the Gene Locus Encoding the Phosphatidylglycerophosphate Synthase of *Escherichia coli*," *The Journal of Biological Chemistry*, Jan. 25, 1986, pp. 1329-1338, vol. 261(3).
Kawasaki, K., et al., "Isolation of a Chinese Hamster Ovary (CHO) cDNA Encoding Phosphatidylglycerophosphate (PGP) Synthase, Expression of Which Corrects the Mitochondrial Abnormalities of a PGP Synthase-Defective Mutant of CHO-K1 Cells," *The Journal of Biological Chemistry*, Jan. 15, 1999, pp. 1828-1834, vol. 274(3).
BIOSIS Database Report for Accession No. PREV197866057954, 1978 (XP002180326).

*Primary Examiner*—P. Achutamurthy
*Assistant Examiner*—Yong D. Pak
(74) *Attorney, Agent, or Firm*—Millennium Pharmaceuticals, Inc.

(57) ABSTRACT

The present invention relates to a newly identified human PGP synthase. The invention also relates to polynucleotides encoding the PGP synthase. The invention further relates to methods using the PGP synthase polypeptides and polynucleotides as a target for diagnosis and treatment in PGP synthase-mediated or -related disorders. The invention further relates to drug-screening methods using the PGP synthase polypeptides and polynucleotides to identify agonists and antagonists for diagnosis and treatment. The invention further encompasses agonists and antagonists based on the PGP synthase polypeptides and polynucleotides. The invention further relates to procedures for producing the PGP synthase polypeptides and polynucleotides.

9 Claims, 6 Drawing Sheets

```
Input file Fbh27411fl.seq; Output File 27411.trans
Sequence length 2686
ATCCACGCTTTTGCNTGACCCTTGCTTGGTTCAACTTANAGGTCTTTGTTTCGGTTTTCTTGTTNNGCNCCGGTTACAG

ATCCAAAGTTTTGAAAAAAACCANAAAAGTNANCTGGTAAGTTAAGTCTTTTTTGTCTTTTATTTCCAGNTCCNGGAATC

CGGGTGGTTGGTGCAAANTCAAAAGANTTGTTCCTCAAGTGAATGTTGCNTTTACTTCTTAGGCNTCTACGGAAAGTGT

TATTTTTGTTTTAAAAGCTGGGAATTCTTANTACGACTTCACTATAGGGAGTCGACCCACGCGTCCGGCGAGTCTCC
```

```
         M   A   V   A   A   A   A   A   G   P   V   F   W   R   R   L   L   G   L       20
         ATG GCG GTG GCG GCG CCA GCT GCG GCG GGA CCC GTG TTC TGG AGG CGA CTG CTG GGC CTC   60

L   P   G   R   P   G   L   A   A   L   L   G   R   L   S   D   R   L   G   R    40
         CTG CCT GGC CGC CCA GGG CTG GCC GCG CTC CTG GGA CGC CTG TCC GAC CGC CTC GGC AGG  120

N   R   D   R   Q   R   R   R   S   P   W   L   L   L   A   P   L   L   S   P    60
         AAC CGG GAC CGC CAG CGC AGG AGG TCA CCA TGG CTG TTA TTG GCT CCC TTG CTG TCC CCA  180

A   V   P   Q   V   T   S   P   P   C   C   L   C   P   E   G   V   H   R   F    80
         GCT GTT CCC CAG GTC ACC TCC CCA CCT TGC TGC CTG TGT CCA GAA GGC GTG CAC CGG TTC  240

Q   W   I   R   N   L   V   P   E   F   G   V   S   S   S   H   V   R   V   L   100
         CAG TGG ATC AGA AAC CTG GTT CCA GAA TTT GGA GTC TCC AGT TCT CAC GTT AGG GTG CTT  300

S   S   P   A   E   F   F   E   L   M   K   G   Q   I   R   V   A   K   R   R   120
         TCT TCC CCG GCA GAG TTT TTC GAG CTC ATG AAG GGG CAG ATA AGA GTA GCC AAG AGG CGG  360

V   V   M   A   S   L   Y   L   G   T   G   P   L   E   Q   E   L   V   D   C   140
         GTC GTG ATG GCA TCC CTC TAC CTG GGG ACA GGT CCT TTG GAA CAG GAG CTG GTG GAC TGC  420

L   E   S   T   L   E   K   S   L   Q   A   K   F   P   S   N   L   K   V   S   160
         CTG GAA AGT ACT CTA GAA AAG TCA CTC CAA GCA AAG TTT CCT TCA AAT CTC AAG GTC TCC  480

I   L   L   D   F   T   R   G   S   R   G   R   K   N   S   R   T   M   L   L   180
         ATT CTC TTA GAC TTC ACG CGG GGC TCA CGA GGT CGG AAG AAC TCC CGC ACA ATG CTG CTC  540

P   L   L   R   R   F   P   E   Q   V   R   V   S   L   F   H   T   P   H   L   200
         CCA CTC CTG CGG AGG TTC CCA GAG CAG GTC CGA GTC TCC CTC TTT CAC ACG CCG CAC CTC  600

R   G   L   L   R   L   L   I   P   E   R   F   N   E   T   I   G   L   Q   H   220
         CGT GGG CTG CTT CGG CTC CTC ATC CCT GAG CGC TTC AAC GAG ACC ATC GGC CTC CAG CAC  660

I   K   V   Y   L   F   D   N   S   V   I   L   S   G   A   N   L   S   D   S   240
         ATT AAG GTG TAC CTC TTC GAC AAC AGC GTC ATC TTG AGC GGT GCA AAC CTG AGT GAC TCC  720

Y   F   T   N   R   Q   D   R   Y   V   F   L   Q   D   C   A   E   I   A   D   260
         TAC TTC ACC AAC CGC CAG GAC CGC TAC GTG TTC CTG CAG GAC TGT GCG GAG ATT GCC GAC  780

F   F   T   E   L   V   D   A   V   G   D   V   S   L   Q   L   Q   G   D   D   280
         TTC TTC ACG GAG CTG GTG GAC GCG GTG GGG GAT GTG TCC CTG CAG CTG CAG GGG GAC GAC  840

T   V   Q   V   V   D   G   M   V   H   P   Y   K   G   D   R   A   E   Y   C   300
         ACG GTG CAG GTG GTG GAT GGG ATG GTG CAT CCT TAC AAA GGG GAC CGG GCC GAG TAC TGC  900

K   A   A   N   K   R   V   M   D   V   I   N   S   A   R   T   R   Q   Q   M   320
         AAG GCA GCC AAT AAG AGG GTC ATG GAT GTG ATC AAC TCA GCC AGG ACC CGC CAG CAG ATG  960

```
                                                     CTG CAT GCC CAG ACC TTC CAC AGC AAC TCT CTT TTG ACC CAG GAA GAT CCA GCA GCT GCT  1020
 G   D   R   R   P   A   P   D   T   W   I   Y   P   L   I   Q   M   K   P   F   360
GGG GAT CGC AGA CCA GCC CCT GAC ACC TGG ATT TAT CCG CTG ATT CAG ATG AAG CCC TTC  1080
 E   I   Q   I   D   E   I   V   T   E   T   L   L   T   E   A   E   R   G   A   380
GAG ATT CAA ATC GAT GAG ATT GTC ACT GAG ACC CTG TTG ACT GAG GCG GAG CGC GGG GCA  1140
 K   V   Y   L   T   T   G   Y   F   N   L   T   Q   A   Y   M   D   L   V   L   400
AAG GTC TAC CTC ACC ACT GGC TAT TTC AAC CTG ACC CAG GCC TAC ATG GAC CTG GTC TTG  1200
 G   T   R   A   E   Y   Q   I   L   L   A   S   P   E   V   N   G   F   F   G   420
GGC ACT CGG GCT GAG TAC CAG ATC CTG CTG GCC TCA CCA GAG GTG AAT GGC TTC TTT GGG  1260
 A   K   G   V   A   G   A   I   P   A   A   Y   V   H   I   E   R   Q   F   F   440
GCC AAG GGG GTG GCC GGC GCC ATC CCA GCG GCC TAT GTG CAC ATC GAG CGA CAG TTC TTC  1320
 S   E   V   C   S   L   G   Q   Q   E   R   V   Q   L   Q   E   Y   W   R   R   460
AGT GAG GTG TGC AGC CTG GGA CAG CAG GAG CGG GTG CAG CTT CAG GAG TAC TGG CGG AGG  1380
 G   W   T   F   H   A   K   G   L   W   L   Y   L   A   G   S   S   L   P   C   480
GGC TGG ACG TTC CAC GCC AAA GGC CTC TGG CTG TAC CTG GCA GGG AGC AGC CTG CCC TGT  1440
 L   T   L   I   G   S   P   N   F   G   Y   R   S   V   H   R   D   L   E   A   500
CTC ACG CTG ATT GGC TCT CCT AAT TTT GGG TAC AGG TCA GTT CAC CGG GAC CTG GAG GCC  1500
 Q   I   A   I   V   T   E   N   Q   A   L   Q   Q   Q   L   H   Q   E   Q   E   520
CAG ATT GCG ATC GTG ACG GAG AAC CAG GCC CTG CAG CAG CAG CTT CAC CAG GAG CAA GAG  1560
 Q   L   Y   L   R   S   G   V   V   S   S   A   T   F   E   Q   Q   S   R   Q   540
CAG CTC TAC CTG AGG TCA GGT GTG GTG TCC TCT GCC ACC TTC GAG CAG CGG AGT CGC CAG  1620
 V   K   L   W   V   K   M   V   T   P   L   I   K   N   F   F   *           557
GTG AAG CTG TGG GTG AAG ATG GTG ACT CCA CTG ATC AAG AAC TTC TTC TGA           1671
```

GGACAGACAGGTGCTGTCTCTAGCATCACCTCTCAGCACGATTTTCCCGAGAGTTCACAGGAATGGCCTTGATGAAGAT
GACAGGCATGGCCGGGGTCAGCTCTTTCAGCCGCGCTTCAGCGATGACTCCAGTCTGGGTGTCCAGCGAGCCCCTGCA
GGGACAGTATGGCTGAGGGTCAGGTGTGCTGCCAGTAAGTGAGGGAGGGGCTGGCAGGAAGGGTGGGGTCCTCACACTC
CCCGCCCTYTGCAGAGCTGGGCTCTACCCCAAAAGGCTTCAGGCCAGCTGCCACAGCTGGAAGCAGAGGCCTTCGTAGG
TGATGGCCTGCATGTTGTAACTACCCCGTCCCGCTGGGCTCAAGGAACAGCTCAGCTAAAGCCCTGGGTTCCATCCGT
TTAAATCTGTGGCATTTTCAGAGCCTCATCTGTCAGCCTTAATGTCAGTGGCAGGAAGTCATAACTCCAGCTAAAAATT
ACAGAGTAAAGTTCCCTGATTCTTAATGTGTAATGTCTGCCCTATGTGTACATACACAATATAATTATACATCTGTGCA
TATAAATATTGCCTTTAACCAGACTGCTATTATTTCTACTGCCCTATTTAATGGTGTTTTATTTCCTGTCTGAAATC
TCAAAATAAACAAACCATGGAGAGCTTAAAAAAAAAAAAAACGGCGGCCGCTAGACTAGTCTAGAGAAA

*FIG. 1B.*

PROSITE PATTERN MATCHES FOR 27411

>PS00001 | PDOC00001 | ASN_GLYCOSYLATION N-glycosylation site.

Query:  213  NETI  216
Query:  236  NLSD  239
Query:  390  NLTQ  393

>PS00004 | PDOC00004 | CAMP_PHOSPHO_SITE cAMP- and cGMP-dependent protein kinase phosphorylation site.

Query:   46  RRRS   49
Query:  172  RKNS  175

>PS00005 | PDOC00005 | PKC_PHOSPHO_SITE Protein kinase C phosphorylation site.

Query:   35  SDR   37
Query:  243  TNR  245
Query:  313  SAR  315

>PS00006 | PDOC00006 | CK2_PHOSPHO_SITE Casein kinase II phosphorylation site.

Query:  102  SPAE  105
Query:  143  STLE  146
Query:  333  TQED  336
Query:  374  TEAE  377
Query:  402  TRAE  405

>PS00007 | PDOC00007 | TYR_PHOSPHO_SITE Tyrosine kinase phosphorylation site.

Query:  344  RPAPDIWIY  352

>PS00008 | PDOC00008 | MYRISTYL N-myristoylation site.

Query:   19  GLLPGR   24
Query:   91  GVSSSH   96
Query:  234  GANLSD  239
Query:  423  GVAGAI  428
Query:  527  GVVSSA  532

>PS00009 | PDOC00009 | AMIDATION Amidation site.

Query:  170  RGRK  173

FIG. 4.

27411, A NOVEL HUMAN PGP SYNTHASE

CROSS-REFERENCE TO RELATED APPLICATION

This application is a divisional application of U.S. Utility application Ser. No. 09/795,691, filed Feb. 28, 2001, now issued as U.S. Pat. No. 6,465,230, which claims the benefit of U.S. Provisional Application Ser. No. 60/185,517 filed Feb. 28, 2000, both of which are hereby incorporated in their entirety by reference

FIELD OF THE INVENTION

The present invention relates to newly identified human phosphatidyl-gycerolphosphate (PGP) synthase belonging to the family of mammalian PGP synthases. The invention also relates to polynucleotides encoding the PGP synthase. The invention further relates to methods using the PGP synthase polypeptides and polynucleotides as a target for diagnosis and treatment in PGP synthase-mediated or -related disorders. The invention further relates to drug-screening methods using the PGP synthase polypeptides and polynucleotides to identify agonists and antagonists for diagnosis and treatment. The invention further encompasses agonists and antagonists based on the PGP synthase polypeptides and polynucleotides. The invention further relates to procedures for producing the PGP synthase polypeptides and polynucleotides.

BACKGROUND OF THE INVENTION

Cardiolipin is a dimeric phospholipid which plays an important role in mitochondrial biogenesis and function. It is required for activity of several mitochondrial enzymes and possibly for the transport of proteins into the mitochondria in eukaryotes (Minskoff, S. et al. (1997) *Biochimica et Biophysica Acta* 1348: 187–191). Cardiolipin appears to be involved either directly or indirectly, in the modulation of a number of cellular processes including the activation of mitochondrial enzymes and the production of energy by oxidative phosphorylation (Hatch, G. (1998) *International J. of Mol. Medicine* 1: 33–41).

Cardiolipin is found in animals, plants, and fungi. In mammals it is found exclusively in mitochondria. Cardiolipin is the principal polyglycerophospholipid found in the heart and most mammalian tissues (Hatch, G. (1998) *International J. of Molec. Medicine* 1:33–41). The biosynthetic pathway of cardiolipin has been well studied in yeasts. The first enzyme in the cardiolipin biosynthetic pathway is phosphatidylglycerolphosphate synthase (PGP synthase). PGP synthase is a key enzyme in the pathway as it catalyzes the committed first step in the pathway.

The biosynthesis of cardiolipin occurs in 3 enzymatic steps. In the first step, PGP synthase catalyzes the formation of phosphatidylglycerolphosphate (PGP) from phosphatidyl-CMP (CDP-diacylglycerol, CDP-DG) and glycerol 3-phosphate. PGP is then dephosphorylated to phosphatidylglycerol (PG) by PGP phosphatase. Finally, in eukaryotes cardiolipin is synthesized from PG and another molecule of CDP-DG in a reaction catalyzed by cardiolipin synthase.

Cardiolipin appears to be essential for the function of several enzymes of oxidative phosphorylation. (Hatch, G. (1996) *Molecular and Cellular Biochemistry* 159:139–148). Also, cardiolipin has been implicated in the role of many enzymatic activities, including but not limited to: (1) cytochrome c oxidase, (2) carnitine acylcarnitine translocase, (3) mitochondrial protein import, and (4) binding of matrix $Ca^{+2}$ (Kawasaki, K. (1999) *J. of Biological Chemistry*, Vol. 274, No.3, 1828–1834).

There must be stringent levels of control of the enzymes involved in cardiolipin metabolism in the heart in order to maintain the appropriate content and molecular species composition of the phospholipid. The maintenance of cardiolipin content and molecular composition in cardiac mitochondria is essential for proper cardiac function (Hatch, G. (1998) *International J. of Mol. Medicine* 1:33–41).

Phosphatidylglycerol (PG) and cardiolipin (CL) are the most widely distributed glycerophosphatides in the membrane lipids of animals, plants and microbes (Hostletler, K. Y. (1982) in *Phospholipids* (Hawthorne and Ansell, eds) pp.215–261, Elsevier/North Holland Biomedical Press, Amsterdam).

PG is localized in many intracellular locations as a component of phospholipids, representing less than 1% of total lipid phosphorous, except in the lung where it represents about 10% of the total phospholipids (Mason, R. J. et al., (1980) *Biochim. Biophys. Acta* 617: 36–50). PG serves as an important component of the pulmonary surfactant in the lung (Ohtsuka et al., (1993) *J. Biol Chem.* Vol. 268: 22908–22913). CL is localized primarily in the mitochondria and appears to be essential for the function of several enzymes of oxidative phosphorylation. CL is essential for production of energy for the heart to beat (Hatch, G. M. (1996) *Molecular and Cellular Biochemistry*, 159: 139–148).

PGP synthase has been extensively studied and characterized in two evolutionarily divergent yeasts, *Saccharomyces cerevisiae* and *Schizosaccharomyces pombe*. PGP synthase has been purified to homogeneity from *S. pombe* (Minskoff, S. et al. (1997) *Biochimica et Biophysica Acta* 1348: 187–191). In contrast to the second and third enzymes of the cardiolipin biosynthetic pathway, PGP synthase activity is highly regulated both by cross-pathway control and by factors affecting mitochondrial development.

PGP synthase has been shown to be controlled by two sets of factors: cross-pathway control and factors affecting mitochondrial development. Cross-pathway control of phosphatidylinositol and phosphatidylcholine control is characterized by three parameters. First, the availability of the water-soluble phospholipid precursor inositol controls expression of phospholipid biosynthetic enzymes. Second, inositol repression of phospholipid biosynthesis occurs only if cells can synthesize phosphatidyl-choline. Third, inositol repression is mediated by the INO2-INO4-OPI1 regulatory genes. PGP synthase is regulated by inositol. However, it is not subject to control by the INO2-INO4-OPI1 regulatory genes. PGP synthase activity is decreased 3–5 fold in *Saccharomyces cerevisiae* cells grown in the presence of inositol (Greenberg, M. L. et al., (1988) *Mol. Cell. Biol.* 8: 4773–4779).

PGP synthase is commonly referred to as glycerophosphate phosphatidyl-transferase (E. C. 2.7.8.5). It catalyzes a substituted phospho group transfer. The natural substrate of the enzyme is CDP-1,2-diacyl-sn-glycerol and glycerol 3-phosphate (involved in the synthesis of phosphatidylgylcerol). Different cofactors and prosthetic groups which have been shown to be important for maximal PGP synthase activity include, but are not limited to: Triton X-100, phosphatidylethanolamine and phosphatidylinositol. Different metal/salts which have been shown to be important for PGP synthase activity include, but are not limited to: $Mn^{+2}$, $Mg^{+2}$, $Ca^{+2}$, $Co^{+2}$, and $Ba^{+2}$.

PGP synthases in two different yeasts (*S. cerevisiae* and *S. pombe*) were found to be sensitive to thioreactive compounds and have a requirement for divalent cations (Minskoff, S. et al. (1997) *Biochimica et Biophysica Acta* 1348: 187–191).

Inhibitors of PGP synthase have been shown to include, but are not limited to: liponucleotide, CDPdiacylglycerol, glycerol 3-phosphate, thioreactive agents, calcium, inositol, Triton X-100, magnesium, cadmium, zinc, copper, and mercury (see www.expasy.ch/cgi-bin/enzyme-search-ec). As one example, PGP synthase activity was shown to decrease 3 to 5 fold in *S. cerevisiae* cells grown in the presence of inositol.

PGP synthase activity can be assayed by determining the conversion of $[^{14}C(U)]$ glycerol 3-phosphate to phosphatidyl $[^{14}C(U)]$glycerol 3-phosphate as described by Cao et al. (Cao et al. (1994) *LIPIDS,* Vol. 29, no.7, pp.475–480).

Chinese hamster ovary (CHO) cells defective in PGP synthase production have been studied to better elucidate the role of the enzyme in the biosynthesis of PG and CL (Ohtsuka, T. et al., (1993) *J. Biol. Chem.* Vol.268, No. 30, pp. 22908–22913). Ohtsuka et al. developed a rapid autoradiographic screening assay for detecting PGP synthase activity in the lysates of Chinese hamster ovary cell colonies immobilized on polyester, as described by Raetz et al. (Raetz et al., (1982) *Proc. Natl. Acad. Sci. U.S.A.* 79: 3223–3227). The Ohtsuka study confirmed the role of PGP synthase in the biosynthesis of PG and its essential role in the growth of CHO cells. The results provided direct evidence for the formation of PG in vivo and that PG is a major metabolic precursor for the biosynthesis of cellular CL.

Recent research has focused on the generation of a PGP-synthase defective mutant in CHO-K1 cells (Kawasaki, K. et al. (1999) *J. Biol. Chem.* Vol. 274:1828–1834). Kawasaki et al. isolated a Chinese hamster ovary (CHO) cDNA encoding a putative protein similar in sequence to the yeast PGS1 gene product, PGP synthase. The CHO PGS1 cDNA encoded a protein having high amino acid homology with the yeast PGS1. Transfection of CHO-K1 cells with CHO PGS1 cDNA in *E.coli* resulted in a highly elevated PGP synthase activity level. Moreover, when the CHO PGS1 was introduced into a mutant PGS-S (a temperature-sensitive mutant defective in PGP synthase), the mutant recovered normal biosynthesis and cellular content of PG and CL. The results demonstrated the CHO PGS1 cDNA encodes a PGP synthase. (Kawasaki, K. et al. (1999) *J. Biol. Chem.* Vol. 274, No.3, pp. 1 828–1834). The cloned CHO PGS1 cDNA was able to complement the mitochondrial defect as well as the biosynthetic defects in CL and PG biosynthesis.

Moreover, there is an apparent difference in the molecular mechanisms of the PGP synthases between eukaryotic and prokaryotic organisms. The eukaryotic PGP synthases most likely utilize a ping-pong reaction mechanism, in contrast to the prokaryotic PGP synthases that employ a bi-bi reaction mechanism (Dryden, S. (1996) *J. Bacteriol.* 178: 1030–1038). PGP synthase is an essential enzyme in bacteria (Heacock, P. N. et al., (1987) *J. Biol. Chem.* 262: 13044–13049). Presumably, this difference in reaction mechanism between eukaryotic and prokaryotic PGP synthases might represent a target for antibacterial agents (Kawasaki, K. et al. (1999) *J. Biol. Chem.* Vol. 274, No.3, pp. 1828–1834).

PGP synthases are important as relates to cardiolipin metabolism in aging and thyroid dysfunction. Aging and hypothyroidism are two conditions associated with mitochondrial dysfunction and cardiolipin deficiency. (Schlame, M. et al., (1997) *Biochimica et Biophysica Acta,* 1348: 207–213). In both cases, mitochondrial cardiolipin deficiency could be correlated with a decrease in metabolite transport activity across mitochondrial membrane. As relates to the aging process, it has been suggested that cardiolipin deficiency is the cause of reduced metabolite transport due to changes in the membrane environment of the carrier proteins (Paradies et al. (1992) *Biochim. Biophys. Acta* 1103: 324–326).

Conversely, hyperthyroidism is characterized by mitochondria with increased cardiolipin content and increased metabolite transport activities (Paradies (1990) *Biochim. Biophys. Acta* 1019:133–136). Thyroxine is a well-known stimulator of mitochondrial biogenesis; it is known to increase the number of mitochondria as well as enhance their performance.

Accordingly, PGP synthases are a major target for drug action and development. Accordingly, it is valuable to the field of pharmaceutical development to identify and characterize novel PGP synthases and tissues and disorders in which PGP synthases are differentially expressed. The present invention advances the state of the art by providing a novel human PGP synthase and tissues and disorders in which expression of the human PGP synthase is relevant. Accordingly, the invention provides methods directed to expression of the PGP synthase.

SUMMARY OF THE INVENTION

It is an object of the invention to identify a novel PGP synthase.

It is a further object of the invention to provide novel PGP synthase polypeptides that are useful as reagents or targets in assays applicable to treatment and diagnosis of PGP synthase-mediated or -related disorders.

It is a further object of the invention to provide polynucleotides corresponding to the novel PGP synthase polypeptides that are useful as targets and reagents in PGP synthase assays applicable to treatment and diagnosis of PGP synthase-mediated or -related disorders and useful for producing novel PGP synthase polypeptides by recombinant methods.

A specific object of the invention is to identify compounds that act as agonists and antagonists and modulate the expression of the novel PGP synthase.

A further specific object of the invention is to provide compounds that modulate expression of the PGP synthase for treatment and diagnosis of PGP synthase -related disorders.

The invention is thus based on the identification of a novel human PGP synthase. The amino acid sequence for PGP synthase is shown in SEQ ID NO:2. The nucleotide sequence for PGP synthase is shown in SEQ ID NO:1.

The invention provides isolated PGP synthase polypeptides, including a polypeptide having the amino acid sequence shown in SEQ ID NO:2, or the amino acid sequences encoded by the cDNAs deposited as Patent Deposit Nos. PTA-2011 and PTA-2340.

The invention also provides isolated PGP synthase nucleic acid molecules having the sequence shown in SEQ ID NO:1, SEQ ID NO:3, or in the deposited cDNAs.

The invention also provides variant polypeptides having an amino acid sequence that is substantially homologous to the amino acid sequence shown in SEQ ID NO:2 or encoded by the deposited cDNAs.

The invention also provides variant nucleic acid sequences that are substantially homologous to the nucleotide sequence shown in SEQ ID NO:1 or in the deposited cDNAs.

The invention also provides fragments of the polypeptides shown in SEQ ID NO:2 and nucleotide sequence shown in SEQ ID NO:1 as well as substantially homologous fragments of the polypeptides or nucleic acids.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the PGP synthase nucleic acid molecules and polypeptides, and particularly recombinant vectors and host cells.

The invention also provides methods of making the vectors and host cells and methods for using them to produce the PGP synthase nucleic acid molecules and polypeptides.

The invention also provides antibodies or antigen-binding fragments thereof that selectively bind the PGP synthase polypeptides and fragments.

The invention also provides methods of screening for compounds that modulate expression or activity of the PGP synthase polypeptides or nucleic acid (RNA or DNA).

The invention also provides a process for modulating PGP synthase polypeptide or nucleic acid expression or activity, especially using the screened compounds. Modulation may be used to treat conditions related to aberrant activity or expression of the PGP synthase polypeptides or nucleic acids.

The invention also provides assays for determining the activity of or the presence or absence of the PGP synthase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the nucleotide sequence (SEQ ID NO:1) and the deduced amino acid sequence (SEQ ID NO:2) of the novel PGP synthase. The PGP synthase coding sequence, nucleotides 315–1985 of SEQ ID NO:1, constitutes SEQ ID NO:3.

FIG. 4 shows an analysis of the PGP synthase open reading frame for amino acids (SEQ ID NO:2) corresponding to specific functional sites. N-glycosylation sites are found from about amino acid 213 to about amino acid 216, from about amino acid 236 to about amino acid 239, and from about amino acid 390 to about amino acid 393. Cyclic AMP and cGMP-dependent protein kinase phosphorylation sites are found from about amino acid 46 to about amino acid 49 and from about amino acid 172 to about 175. Protein kinase C phosphorylation sites are found from about amino acid 35 to about amino acid 37, from about amino acid 243 to about amino acid 245, and from about amino acid 313 to about amino acid 315. Casein kinase II phosphorylation sites are found from about amino acid 102 to about amino acid 105, from about amino 143 to about amino acid 146, from about amino acid 333 to about amino acid 336, from about amino acid 374 to about amino acid 377, and from about amino acid 402 to about amino acid 405. A tyrosine kinase phosphorylation site is found from about amino acid 344 to about amino acid 352. N-myristoylation sites are found from about amino acid 19 to about amino acid 24, from about amino acid 91 to about amino acid 96, from about amino acid 234 to about amino acid 239, from about amino acid 423 to about amino acid 428, and from about amino acid 527 to about amino acid 532. An amidation site is found from about amino acid 170 to about amino acid 173.

DETAILED DESCRIPTION OF THE INVENTION

Figure 2:
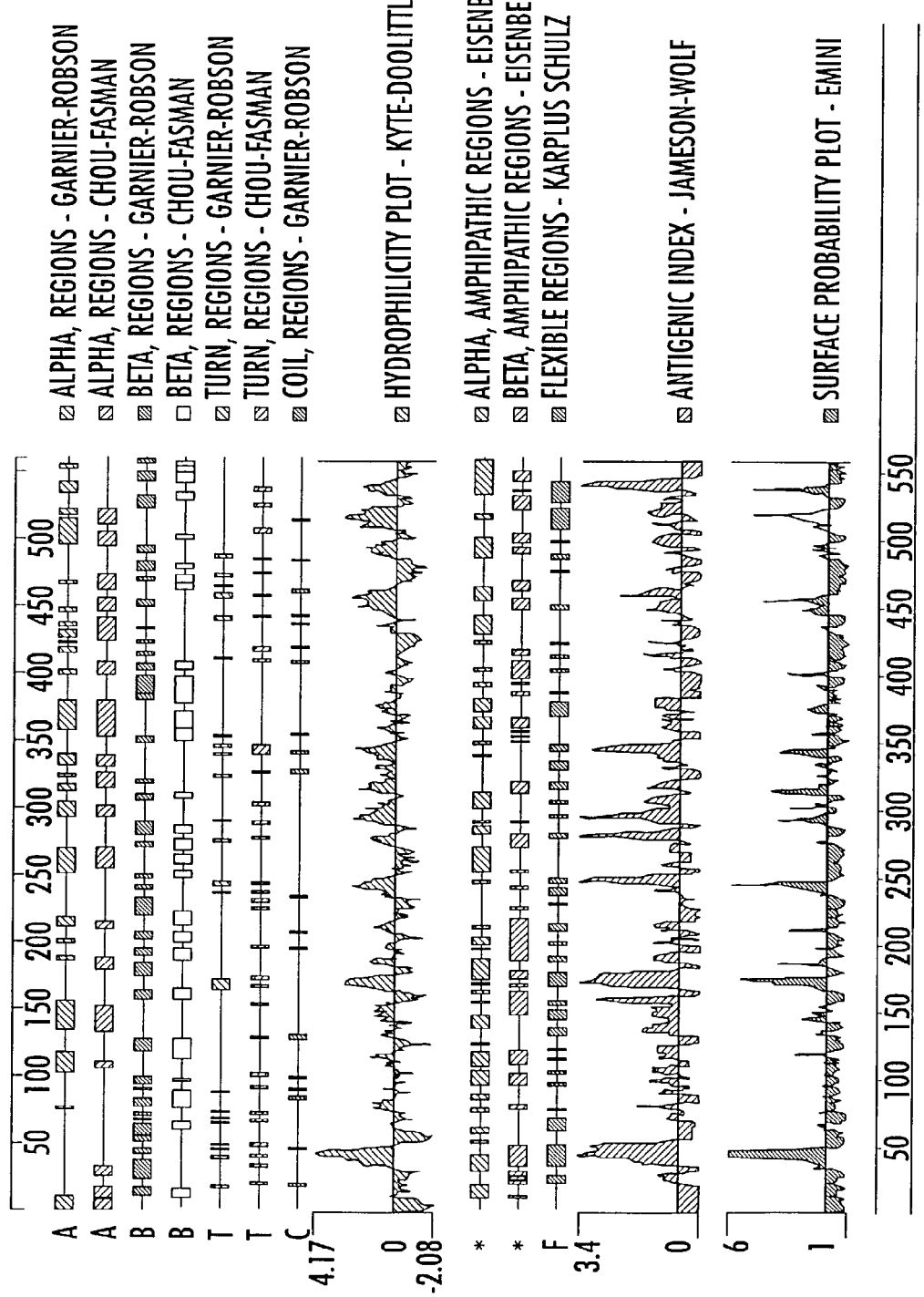
FIG. 2 shows an analysis of the PGP synthase amino acid sequence: αβturn and coil regions; hydrophilicity; amphipathic regions; flexible regions; antigenic index; and surface probability plot.
Figure 3:
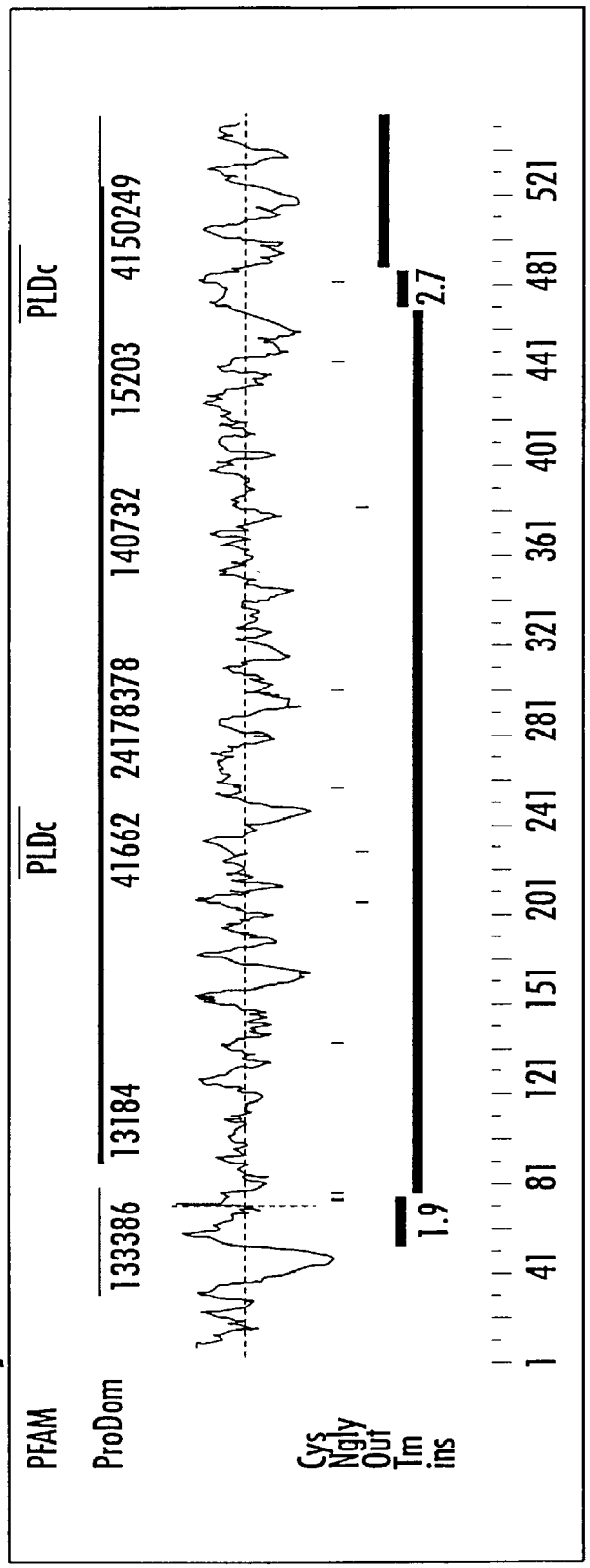
FIG. 3 shows a hydrophobicity plot of the PGP synthase amino acid sequence (SEQ ID NO:2). Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human 27411 are indicated. Polypeptides of the invention include fragments which include: all or a part of a hydrophobic sequence (a sequence above the dashed line); or all or a part of a hydrophilic fragment (a sequence below the dashed line). Other fragments include a cysteine residue or an N-glycosylation site. A signal peptide is predicted from about amino acid 1 to about amino acid 68. Also shown are the predicted transmembrane segments of the full length protein from about amino acid 51 to about amino acid 73 and from about amino acid 469 to about amino acid 485. A predicted transmembrane segment for the presumed mature peptide is from about amino acid 402 to about amino acid 418.

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference for the purpose of describing and disclosing cell lines, vectors, and methodologies which are reported in the publications which might be used in connection with the invention. Nothing is to be construed as an admission that the invention is not entitled to antedate such disclosure by virtue of prior invention.

"Nucleic acid sequence" as used herein, refers to an oligonucleotide, nucleotide, or polynucleotide, and fragments and portions thereof, and to DNA or RNA of genomic or synthetic origin which may be single-or double-stranded, and represents the sense or antisense strand. Similarly, "amino acid sequence" as used herein refers to an oligopeptide, peptide, polypeptide, or protein sequence, and fragments or portions thereof, and to naturally occurring, recombinant or synthetic molecules.

Where "amino acid sequence" is recited herein to refer to an amino acid sequence of a naturally occurring protein molecule, amino acid sequence and like terms, such as "polypeptide" or "protein" are not meant to limit the amino acid sequence to the complete, native amino acid sequence associated with the recited protein.

PGP synthase as used herein, refers to the amino acid sequences of substantially purified PGP synthase obtained from any species, particularly mammalian, including bovine, ovine, porcine, murine, equine, and preferably human, from any source whether natural, synthetic, semisynthetic, or recombinant.

A "deletion" as used herein, refers to a change in either amino acid or nucleotide sequence in which one or more amino acids or nucleotide residues, are absent.

An "insertion" or "addition", as used herein, refers to a change in an amino acid or nucleotide sequence resulting in the addition of one or more amino acid or nucleotide residues.

A "substitution" as used herein, refers to the replacement of one or more amino acids or nucleotides by different amino acids or nucleotides, respectively.

The term "biologically active" as used herein, refers to a protein having structural, regulatory, or biochemical functions of the PGP synthase. Also "immunologically" active refers to the capability of the natural, recombinant, or synthetic PGP synthase, or any oligopeptide thereof, to induce a specific immune response in appropriate animals or cells and to bind with specific antibodies.

The term "agonist" as used herein, refers to a molecule which, when bound to the synthase causes a change in PGP synthase which modulates activity of PGP synthase. Agonists may include proteins, nucleic acids, carbohydrates or any other molecules.

The terms "antagonist" or "inhibitor", as used herein, refer to a molecule which blocks or modulates the biological activity of PGP synthase. Antagonists may include proteins, nucleic acids, carbohydrates, or any other molecules.

The term "modulate" as used herein, refers to a change in the biological level or activity of PGP synthase. Modulation may be an increase or a decrease in protein activity, a change in binding characteristics of PGP synthase to its substrate or effector molecule, or any other change in the biological, functional, or immunological properties of PGP synthase.

The term "derivative" as used herein, refers to the chemical modifications of a nucleic acid encoding PGP synthase or the encoded PGP synthase. Illustrations of such modifications would be replacement of hydrogen by an alkyl, acyl, or amino group. A nucleic acid derivative would encode a polypeptide which retains essential biological characteristics of the natural molecule.

Polypeptides

The invention is based on the identification of a novel PGP synthase and the polynucleotide sequence encoding the PGP synthase.

The invention thus relates to a novel PGP synthase having the amino acid sequence shown in FIG. 1 or the amino acid sequence shown in SEQ ID NO:2, or the amino acid sequences encoded by the deposited cDNAs as Patent Deposit Nos. PTA-2011 or PTA-2340.

Plasmids containing the nucleotide sequences of the invention were deposited with the Patent Depository of the American Type Culture Collection (ATCC), Manassas, Va., on Jun. 9, 2000 and Aug. 10, 2000 and assigned Patent Deposit Nos. PTA-2011 and PTA-2340, respectively. The deposits will be maintained under the terms of the Budapest Treaty on the International Recognition of the Deposit of Microorganisms. The deposit is provided as a convenience to those of skill in the art and is not an admission that a deposit is required under 35 U.S.C. § 112. The deposited sequences, as well as the polypeptides encoded by the sequence, are incorporated herein by reference and controls in the event of any conflict, such as a sequencing error, with description in this application.

"PGP synthase polypeptide" or "PGP synthase protein" refers to the polypeptide in SEQ ID NO:2, or the polypeptide encoded by the deposited cDNA. The term "PGP synthase protein" or "PGP synthase polypeptide", however, further includes the numerous variants described herein, as well as fragments derived from the full-length PGP synthase and variants. By "variants" is intended proteins or polypeptides having an amino acid sequence that is at least about 60%, 65%, or 70%, preferably about 75%, 85%, 90%, 91%, 92%, 93%, 94%, 95%, 96%, 97%, 98%, or 99% identical to the amino acid sequence of SEQ ID NO:2. Variants also include polypeptides encoded by the cDNA inserts of the plasmids deposited with the ATCC as Patent Deposit Number PTA-2011 or PTA-2340, or polypeptides encoded by a nucleic acid molecule that hybridizes to the nucleic acid molecule of SEQ ID NO:1, SEQ ID NO:3, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants retain the functional activity of the PGP synthase like proteins of the invention. Variants include polypeptides that differ in amino acid sequence due to natural allelic variation or mutagenesis.

PGP synthases are found in most mammalian tissues with the highest concentrations in the heart, lung, and liver (see www.expasy.ch/enzyme).

The present invention thus provides isolated or purified polypeptides of the PGP synthase and variants and fragments thereof.

Based on a Blast search, highest homology to the PGP synthase of the invention was shown to phosphatidylglycerophosphate synthase from *Cricetulus griseus* (Genbank Acc. No. AB016930). The polypeptide of the invention is 93% identical to the *C. griseus* phosphatidylglycerophosphate synthase in the region from amino acids 4 to 556 of SEQ ID NO:2. The nucleotide sequence of the invention is 87% identical to the *C. griseus* phosphatidylglycerophosphate synthase nucleotide sequence in the region from nucleotides 326–1991 of SEQ ID NO:1.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The PGP synthase polypeptides can be purified from mammalian tissues (McMurray, W. C. et al., (1978) *Can J. Biochem.* 56, 414–419). It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the PGP synthase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A PGP synthase polypeptide is also considered to be isolated when it is part of a membrane preparation or is purified and then reconstituted with membrane vesicles or liposomes.

The language "substantially free of chemical precursors or other chemicals" includes preparations of the PGP synthase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the PGP synthase polypeptides comprise the amino acid sequences shown in SEQ ID NO:2. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the PGP synthase of SEQ ID NO:2. Variants also include proteins substantially homologous to the PGP synthase but derived from another organism, i.e., an ortholog. Variants also include proteins that are substantially homologous to the PGP synthase that are produced by chemical synthesis. Variants also include proteins that are substantially homologous to the PGP synthase that are produced by recombinant methods. Variants retain the functional activity of the PGP synthase like polypeptides set forth in SEQ ID NO:2. It is understood, however, that variants exclude any amino acid sequences disclosed prior to the invention.

As used herein, two proteins (or a region of the proteins) are substantially homologous when the amino acid sequences have at least about 60%, 65%, 70%, 75%, 80%, 85%, 90%, 91%, 92%, 93%, 94%, 95%, 96%, 97%, 98%, or 99% identity. A substantially homologous amino acid sequence, according to the present invention, will be encoded by a nucleic acid sequence hybridizing to the nucleic acid sequence, or portion thereof, of the sequence shown in SEQ ID NO:1 or SEQ ID NO:3 under stringent conditions as more fully described below. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:

403–10. BLAST nucleotide searches can be performed with the NBLAST program, score=100, wordlength=12 to obtain nucleotide sequences homologous to the 27411 nucleic acid molecules of the invention. BLAST protein searches can be performed with the XBLAST program, score=50, wordlength=3 to obtain amino acid sequences homologous to the 27411 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See www.ncbi.nlm.nih.gov.

The invention also encompasses polypeptides having a lower degree of identity but having sufficient similarity so as to perform one or more of the same functions performed by the PGP synthase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these. Variant polypeptides can be fully functional or can lack function in one or more activities. Variants include those having alterations that affect interaction with any of the substrates or effector molecules, including but not limited to those disclosed herein or that affect the function of the PGP synthase that normally results from such interaction. For example, variants of the PGP synthase can have an altered binding affinity for the substrates, CDP-diacylglycerol and glycerol 3-phosphate.

Another useful variation provides a fusion protein in which one or more domains or subregions are operationally fused to one or more domains or subregions from another PGP synthase. Specifically, a domain or subregion can be introduced that alters the substrate specificities or the rate of the enzymatic reaction.

Fully functional variants typically contain only conservative variations or variations in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally occurring or can be made by recombinant means or chemical synthesis to provide useful and novel characteristics for the PGP synthase polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for PGP synthase activity, such as the binding affinity for the substrates or determining the catalytic constants for substituted phospho group transfer between CDP-diacylglycerol and glycerol 3-phosphate. Sites that are critical for substrate binding can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

The assays for PGP synthase enzyme activity are well known in the art and can be found for example, in Ohtsuka et al.(1993) *J. Biol. Chem.* Vol. 268, No.30, 22908–22913). Substantial homology can be to the entire nucleic acid or amino acid sequence or to fragments of these sequences.

The invention thus also includes polypeptide fragments of the PGP synthase. Fragments can be derived from the amino acid sequences shown in SEQ ID NO:2. However, the invention also encompasses fragments of the variants of the PGP synthase as described herein.

The fragments to which the invention pertains, however, are not to be construed as encompassing fragments that may be disclosed prior to the present invention. Accordingly, a fragment of the PGP synthase can comprise at least about 20, 25, 30, 40, 50, 100, 150, 200, 250, 300, 350, 400, 450, 500, 550, or 556 contiguous amino acids. Fragments can retain one or more of the biological activities of the protein, for example the ability to bind the substrate or the ability to catalyze the substituted phospho group transfer. Alternatively, fragments can be used as an immunogen to generate PGP synthase antibodies.

Biologically active fragments (peptides which are, for example, 5, 10, 15, 20, 30, 40, 50, 100, 150, 200, 250, 300, 350, 400, 450, 500, 550, or 556 amino acids in length) can comprise a domain or motif including a substrate binding site, catalytic binding site and sites for glycosylation, protein kinase C phosphorylation, Casein kinase II phosphorylation, cyclic AMP and cGMP-dependent phosphorylation, tyrosine kinase phosphorylation and N-myristoylation. Further possible fragments may include sites important for cellular and subcellular targeting.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the PGP synthase or PGP synthase variants. These epitope-bearing peptides are useful to raise antibodies that bind specifically to an PGP synthase polypeptide or region or fragment. These peptides can contain at least 5, 10, at least 15, or between at least about 15 to about 30 amino acids.

Non-limiting examples of antigenic polypeptides that can be used to generate antibodies include but are not limited to peptides derived from an extracellular site. Regions having a high antigenicity index are shown in FIG. 2 for the PGP synthase. However, intracellularly-made antibodies ("intrabodies") are also encompassed, which would recognize intracellular peptide regions.

The epitope-bearing PGP synthase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the PGP synthase fragment and an additional region fused to the carboxyl terminus of the fragment.

The invention thus provides chimeric or fusion proteins. These comprise a PGP synthase peptide sequence operatively linked to a heterologous peptide having an amino acid sequence not substantially homologous to the PGP synthase. "Operatively linked" indicates that the PGP synthase peptide and the heterologous peptide are fused in-frame. The heterologous peptide can be fused to the N-terminus or C-terminus of the PGP synthase or can be internally located. In the case where an expression cassette contains two protein-coding regions joined in a contiguous manner in the same reading frame, the encoded polypeptide is herein defined as a "heterologous polypeptide" or a "chimeric polypeptide" or a "fusion polypeptide". As used herein, a PGP synthase "heterologous protein" or "chimeric protein" or "fusion protein" comprises a PGP synthase polypeptide operatively linked to a non-PGP synthase polypeptide.

In one embodiment the fusion protein does not affect PGP synthase function per se. For example, the fusion protein can be a GST-fusion protein in which the PGP synthase sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant PGP synthase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing an PGP synthase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An PGP synthase-encoding nucleic acid can be cloned into such an expression vector such that the fusion moiety is linked in-frame to the PGP synthase.

Another form of fusion protein is one that directly affects PGP synthase functions. Accordingly, a PGP synthase polypeptide is encompassed by the present invention in which one or more of the PGP synthase domains (or parts thereof) has been replaced by homologous domains (or parts thereof) from another PGP synthase. Accordingly, various permutations are possible. For example, the binding or catalytic domain, or subregion thereof, can be replaced with the domain or subregion from another PGP synthase or another phosphatidyl transferase. Thus, chimeric PGP synthases can be formed in which one or more of the native domains or subregions has been replaced by another.

Additionally, chimeric PGP synthase proteins can be produced in which one or more functional sites is derived from a different PGP synthase or isoform. It is understood however that sites could be derived from other PGP synthases that occur in the mammalian genome but which have not yet been discovered or characterized. Such sites include but are not limited to the catalytic site and substrate binding sites, and other functional sites disclosed herein.

It is further recognized that the nucleic acid sequences of the invention can be altered to contain codons, which are preferred, or non-preferred, for a particular expression system. For example, the nucleic acid can be one in which at least one altered codon, and preferably at least 10%, or 20% of the codons have been altered such that the sequence is optimized for expression in *E. coli,* yeast, human, insect, or CHO cells. Methods for determining such codon usage are well known in the art.

Figure 5:
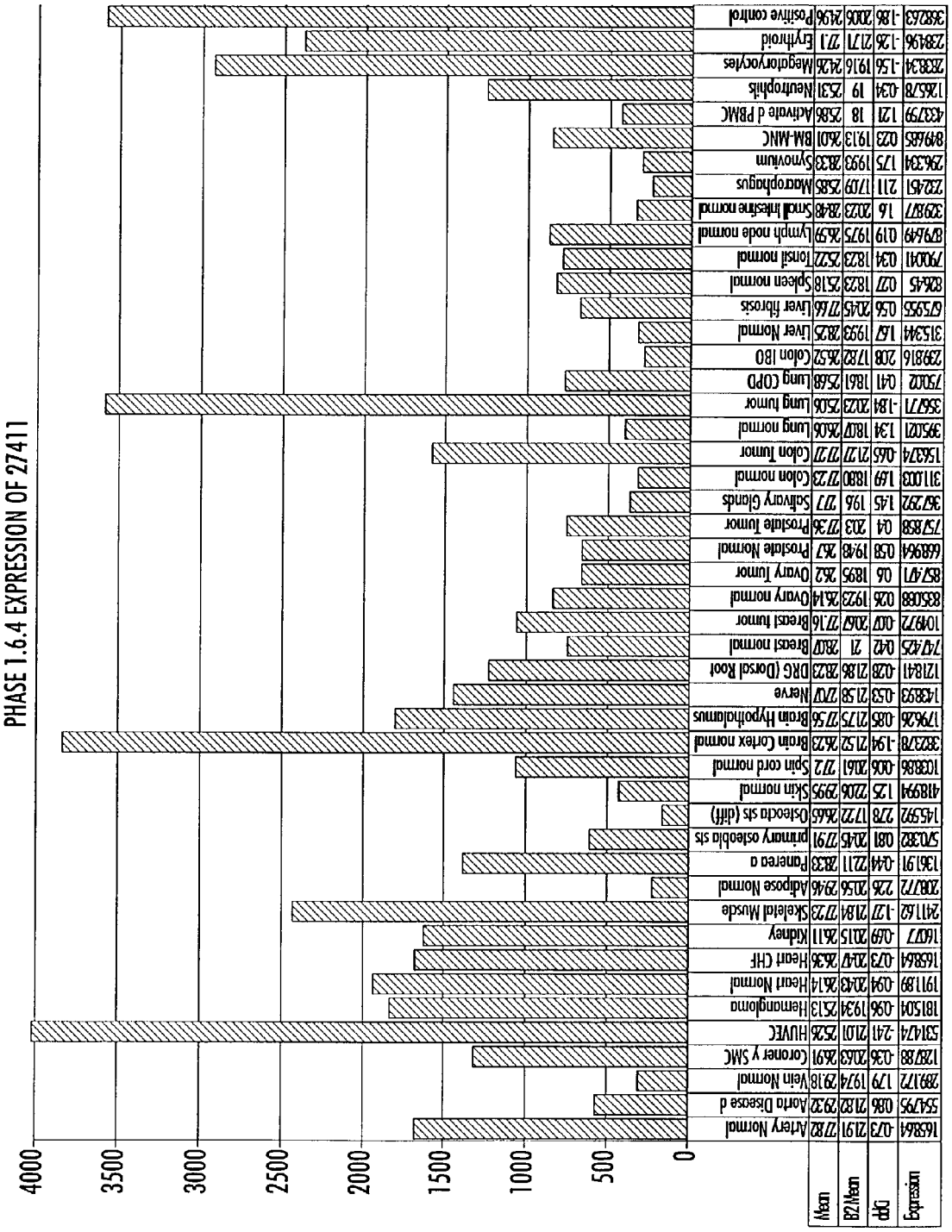
FIG. 5 depicts relative expression of 27411 in various human organs and cell types: artery (column 1), diseased artery (column 2), vein (column 3), coronary smooth muscle cells (column 4), HUVEC (umbilical vein endothelial cells) (column 5), hemangioma (column 6), heart (column 7), congestive heart failure heart (column 8), kidney (column 9), skeletal muscle (column 10), adipose (column 11), pancreas (column 12), primary osteoblasts (column 13), differentiated osteoclasts (column 14), skin (column 15), spinal cord (column 16), brain cortex (column 17), brain hypothalamus (column 18), nerve (column 19), dorsal root ganglion (column 20), breast (column 21), breast tumor (column 22), ovary (column 23), ovarian tumor (column 24), prostate (column 25), prostate tumor (column 26), salivary glands (column 27), colon (column 28), colon tumor (column 29), lung (column 30), lung tumor (column 31), chronic obstructive pulmonary disease lung (column 32), spleen (column 33), tonsil (column 34), lymph node (column 35), small intestine (column 36), macrophages (column 37), synovium (column 38), mononuclear bone marrow cells (column 39), activated peripheral blood mononuclear cells (column 40), neutrophils (column 41), megakaryocytes (column 42), and erythroid tissue (column 43). Tissues or cell types were normal unless indicated otherwise. Expression levels were determined by quantitative RT-PCR (Taqman® brand quantitative PCR kit, Applied Biosystems). These quantitative RT-PCR reactions were performed according to the kit manufacturer's instructions.

The isolated PGP synthase can be purified from cells that naturally express it, including but not limited to heart, lung and liver as well as the tissues shown in FIG. 5. The PGP synthase of the present invention can also be purified from cells that have been altered to express it (recombinant), or synthesized using known protein synthesis methods.

In one embodiment, the protein is produced by recombinant DNA techniques. For example, a nucleic acid molecule encoding the PGP synthase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occuring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The PGP synthase polypeptides are useful for producing antibodies specific for the PGP synthase, regions, or fragments. Regions having a high antigenicity index score are shown in FIG. 2.

The PGP synthase polypeptides are useful for biological assays related to PGP synthase. Such assays involve any of the known PGP synthase functions or activities or properties useful for diagnosis and treatment of PGP synthase-related conditions, including CL and PG biosynthesis.

The PGP synthase polypeptides are also useful in drug screening assays, in cell-based or cell-free systems. Cell-based systems can be native, i.e., cells that normally express the PGP synthase, as a biopsy or expanded in cell culture. In one embodiment, however, cell-based assays involve recombinant host cells expressing the PGP synthase, such as those disclosed in the background above.

Determining the ability of the test compound to interact with the PGP synthase can also comprise determining the ability of the test compound to preferentially bind to the polypeptide as compared to the ability of a known binding molecule (e.g. CDP-diacylglycerol and glycerol 3-phosphate) to bind to the polypeptide.

The polypeptides can be used to identify compounds that modulate PGP synthase activity. Such compounds, for example, can increase or decrease the affinity or rate of binding to the substrates CDP-diacylglycerol and glycerol 3-phosphate, compete with the substrates for binding to the PGP synthase, or displace substrates bound to the PGP synthase. Such compounds can also increase or decrease the enzymatic activity of the PGP synthase. Compounds that modulate PGP synthase activity include, but are not limited to, liponucleotides, CDP diacylglycerol, glycerol 3-phosphate (Hirabayashi et al. (1976) *Biochemistry* 15: 5205–5211), thioreactive agents (Carman et al. (1984) *J. Food Biochem* 8:321–333), inositol (Bleasdale et al. (1982) *Biochim. Biophys. Acta* 710:377–390), and $Ca^{2+}$ (Dowhan et al. (1992) *Methods Enzymol* 71:313–321).

The PGP synthase of the present invention and appropriate variants and fragments can be used in high-throughput screens to assay candidate compounds for the ability to bind to the PGP synthase. These compounds can be further screened against a functional PGP synthase to determine the effect of the compound on the PGP synthase activity. Compounds can be identified that activate (agonist) or inactivate (antagonist) the PGP synthase to a desired degree. Modulatory methods can be performed in vitro (e.g., by culturing the cell with the agent) or, alternatively, in vivo (e.g., by administering the agent to a subject).

The PGP synthase polypeptides can be used to screen a compound for the ability to stimulate or inhibit interaction between the PGP synthase protein and a target molecule that normally interacts with the PGP synthase protein. The target can be a cofactor, metal ion, or PGA synthase substrate. Different cofactors and prosthetic groups which have been shown to be important for maximal PGP synthase activity include, but are not limited to Triton X-100, phosphatidylethanolamine and phosphatidylinositol.

Different metal/salts which have been shown to be important for PGP synthase activity include, but are not limited to $Mn^{+2}$, $Mg^{+2}$, $Ca^{+2}$, $Co^{+2}$, and $Ba^{+2}$. The assay includes the steps of combining the PGP synthase protein with a candidate compound under conditions that allow the PGP synthase protein or fragment to interact with the target molecule, and to detect the formation of a complex between the PGP synthase protein and the target or to detect the biochemical consequence of the interaction with the PGP synthase and the target.

Determining the ability of the PGP synthase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner USP '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length PGP synthase or fragment that competes for substrate binding, including but not limited to those disclosed herein. Other candidate compounds include mutant PGP synthases or appropriate fragments containing mutations that affect PGP synthase function and thus compete for substrates, e.g., CDP-diacylglcerol and glycerol 3-phosphate. Accordingly, a fragment that competes for substrate binding, for example with a higher affinity, or a fragment that binds substrate(s) but does not catalyze the phospho group transfer is encompassed by the invention.

The invention provides other end points to identify compounds that modulate (stimulate or inhibit) PGP synthase activity. The assays typically involve an assay of events that result from a substituted phospho group transfer that indicate PGP synthase activity. Thus, the expression of genes that are up- or down-regulated in response to the PGP synthase enzyme can be assayed. In one embodiment, the regulatory region of such genes can be operably linked to a marker that is easily detectable, such as luciferase. Additionally, measurements of metabolite transport across mitochondrial membranes and mitochondrial cardiolipin content can serve as parameters to quantify PGP synthase activity.

Any of the biological or biochemical functions mediated by the PGP synthase can be used as an endpoint assay. These include all of the biochemical or biological events described herein, in the references cited herein and incorporated by reference for these events, and other PGP synthase functions known to those of ordinary skill in the art.

Binding and/or activating compounds can also be screened by using chimeric PGP synthase proteins in which one or more domains, sites, and the like, as disclosed herein, or parts thereof, can be replaced by their heterologous counterparts derived from other PGP synthases. For example, a substrate binding region or cofactor binding region can be used that interacts with a different substrate or cofactor specificity and/or affinity than the native PGP synthase. Alternatively, a heterologous targeting sequence can replace the native targeting sequence. This will result in different subcellular or cellular localization. As a further alternative, sites that are responsible for developmental, temporal, or tissue specificity can be replaced by heterologous sites such that the PGP synthase can be detected under conditions of specific developmental, temporal, or tissue-specific expression.

The PGP synthase polypeptides are also useful in competition binding assays in methods designed to discover compounds that interact with the PGP synthase. Thus, a compound is exposed to a PGP synthase polypeptide under conditions that allow the compound to bind or to otherwise interact with the polypeptide. Soluble PGP synthase polypeptide is also added to the mixture. If the test compound interacts with the soluble PGP synthase polypeptide, it decreases the amount of complex formed or activity from the PGP synthase target. This type of assay is particularly useful in cases in which compounds are sought that interact with specific regions of the PGP synthase. Thus, the soluble polypeptide that competes with the target PGP synthase region is designed to contain peptide sequences corresponding to the region of interest.

Another type of competition-binding assay can be used to discover compounds that interact with specific functional sites and inhibit PGP synthase. As an example, the substrates (CDP-diacylglycerol and glycerol 3-phosphate) and a candidate compound can be added to a sample of PGP synthase. Compounds that interact with PGP synthase at the same site as the substrates will reduce the amount of complex formed between the PGP synthase and the substrates. One example of a group of compounds that affect PGP synthase activity are thioreactive agents. Additional inhibitors of PGP synthase include: liponucleotide, inositol, Triton X-100, and the divalent cations of magnesium, calcium, cadmium, zinc, mercury, and copper at certain critical millimolar concentrations. (see www.expasy.ch/enzyme).

To perform cell free drug screening assays, it is desirable to immobilize either the PGP synthase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ PGP synthase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of PGP synthase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a PGP synthase-binding target component and a candidate compound are incubated in the PGP synthase-presenting wells and the amount of complex trapped in the well can be quantitated. Methods for detecting such complexes, in addition to those described above for the GST-immobilized complexes, include immunodetection of complexes using antibodies reactive with the PGP synthase target molecule, or which are reactive with PGP synthase and compete with the target molecule; as well as enzyme-linked assays which rely on detecting an enzymatic activity associated with the target molecule.

Modulators of PGP synthase activity identified according to these drug screening assays can be used to treat a subject with a disorder mediated by PGP synthase, by treating cells that express the PGP synthase. These methods of treatment include the steps of administering the modulators of PGP synthase activity in a pharmaceutical composition as described herein, to a subject in need of such treatment. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

The PGP synthases are expressed in tissues including, but not limited to heart, lung, liver, and the tissues shown in FIG. 5.

Hence the PGP synthase of the present invention is relevant to treating disorders involving these tissues.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, a symptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyangiitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the skeletal muscle include tumors such as rhabdomyosarcoma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telangectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the ovary include, for example, polycystic ovarian disease, Stein-Leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, the coma-fibromas, androblastomas, hill cell tumors, and gonadoblastoma; and metastatic tumors such as Krukenberg tumors.

Disorders involving the prostate include, but are not limited to, inflammations, benign enlargement, for example, nodular hyperplasia (benign prostatic hypertrophy or hyperplasia), and tumors such as carcinoma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myclogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma;

erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflanunatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 27411 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

PGP synthases are important as relates to cardiolipin metabolism in the aging process and thyroid dysfunction. Aging and hypothyroidism are two conditions associated with mitochondrial dysfunction and cardiolipin deficiency. (Schlame, M. et al., (1997) *Biochimica et Biophysica Acta,* 1348:207–213). Also, hyperthyroidism is characterized by mitochondria with increased cardiolipin content and increased metabolite transport activities. (Paradies, G. et al., (1992) *Biochim. Biophys. Acta,* 1019:133–136). Therefore, PGP synthases may prove to be useful clinical tools for treating any of these processes and conditions.

The PGP synthase polypeptides are thus useful for treating a PGP synthase-associated disorder characterized by aberrant expression or activity of an PGP synthase. In one embodiment, the method involves administering an agent (e.g., an agent identified by a screening assay described or cited herein), or combination of agents that modulates (e.g., upregulates or downregulates) expression or activity of the protein. In another embodiment, the method involves administering the PGP synthase as therapy to compensate for reduced or aberrant expression or activity of the protein.

Methods for treatment include but are not limited to the use of soluble PGP synthase or fragments of the PGP synthase protein that compete for substrate binding, or interfere with the reaction mediated by the PGP synthase polypeptide. These PGP synthase or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer).

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The PGP synthase polypeptides also are useful to provide a target for diagnosing a disease or predisposition to disease mediated by the PGP synthase, including, but not limited to, diseases involving tissues in which the PGP synthase is expressed, as described herein. Accordingly, methods are provided for detecting the presence, or levels of, the PGP synthase in a cell, tissue, or organism. The method involves contacting a biological sample with a compound capable of interacting with the PGP synthase such that the interaction can be detected.

One agent for detecting PGP synthase is an antibody capable of selectively binding to PGP synthase. A biological sample includes tissues, cells and biological fluids isolated from a subject, as well as tissues, cells and fluids present within a subject.

The PGP synthase also provides a target for diagnosing active disease, or predisposition to disease, in a patient having a variant PGP synthase. Thus, PGP synthase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered PGP synthase activity in cell-based or cell-free assay, alteration in substrate binding, altered substituted phospho group transfer, altered antibody-binding pattern, altered isoelectric point, direct amino acid sequencing, and any other of the known assay techniques useful for detecting mutations in a protein in general or in an PGP synthase specifically.

In vitro techniques for detection of PGP synthase include enzyme linked immunosorbent assays (ELISAs), Western blots, immunoprecipitations and immunofluorescence. Alternatively, the protein can be detected in vivo in a subject by introducing into the subject a labeled anti-PGP synthase antibody. For example, the antibody can be labeled with a radioactive marker whose presence and location in a subject can be detected by standard imaging techniques. Particularly useful are methods, which detect the allelic variant of the PGP synthase expressed in a subject, and methods, which detect fragments of the PGP synthase in a sample.

The PGP synthase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the PGP synthase in which one or more of the PGP synthase functions in one population is different from those in another population. The polypeptides thus allow a target to ascertain a genetic predisposition that can affect treatment modality. Thus, in an PGP synthase-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The PGP synthase polypeptides are also useful for monitoring therapeutic effects during clinical trials and other treatment. Thus, the therapeutic effectiveness of an agent that is designed to increase or decrease gene expression, protein levels or PGP synthase activity can be monitored over the course of treatment using the PGP synthase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the PGP synthase and its variants and fragments. An antibody is considered to selectively bind, even if it also binds to other proteins that are not substantially homologous with the PGP synthase. These other proteins share homology with a fragment or domain of the PGP synthase. This conservation in specific regions gives rise to antibodies that bind to both proteins by virtue of the homologous sequence. In this case, it would be understood that antibody binding to the PGP synthase is still selective.

To generate antibodies, an isolated PGP synthase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 2.

Antibodies are preferably prepared from these regions or from discrete fragments in these regions. However, antibodies can be prepared from any region of the peptide as described herein. A preferred fragment produces an antibody that diminishes or completely prevents substrate or cofactor binding or prevents the transfer of the phospho group. Antibodies can be developed against the entire PGP synthase or domains of the PGP synthase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

An appropriate immunogenic preparation can be derived from native, recombinantly expressed, or chemically synthesized peptides.

Antibody Uses

The antibodies can be used to isolate a PGP synthase by standard techniques, such as affinity chromatography or immunoprecipitation. The antibodies can facilitate the purification of the natural PGP synthase from cells and recombinantly produced PGP synthase expressed in host cells.

The antibodies are useful to detect the presence of PGP synthase in cells or tissues to determine the pattern of expression of the PGP synthase among various tissues in an organism and over the course of normal development.

The antibodies can be used to detect PGP synthase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length PGP synthase can be used to identify PGP synthase turnover.

Further, the antibodies can be used to assess PGP synthase expression in disease states such as in active stages of the disease or in an individual with a predisposition toward disease related to PGP synthase function. When a disorder is caused by an inappropriate tissue distribution, developmental expression, or level of expression of the PGP synthase protein, the antibody can be prepared against the normal PGP synthase protein. If a disorder is characterized by a specific mutation in the PGP synthase, antibodies specific for this mutant protein can be used to assay for the presence of the specific mutant PGP synthase. However, intracellularly-made antibodies ("intrabodies") are also encompassed, which would recognize intracellular PGP synthase peptide regions.

The antibodies can also be used to assess normal and aberrant subcellular localization of cells in the various tissues in an organism. Antibodies can be developed against the whole PGP synthase or portions of the PGP synthase.

The diagnostic uses can be applied, not only in genetic testing, but also in monitoring a treatment modality. Accordingly, where treatment is ultimately aimed at correcting PGP synthase expression level or the presence of aberrant PGP synthase and aberrant tissue distribution or developmental expression, antibodies directed against the PGP synthase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic PGP synthase can be used to identify individuals that require modified treatment modalities.

The antibodies are also useful as diagnostic tools as an immunological marker for aberrant PGP synthase analyzed by electrophoretic mobility, isoelectric point, tryptic peptide digest, and other physical assays known to those in the art.

The antibodies are also useful for tissue typing. Thus, where a specific PGP synthase has been correlated with expression in a specific tissue, antibodies that are specific for this PGP synthase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting PGP synthase function, for example, blocking substrate binding or disrupting transfer of the phospho group between CDP-diacylglycerol and glycerol 3-phosphate.

These uses can also be applied in a therapeutic context in which treatment involves inhibiting PGP synthase function. An antibody can be used, for example, to block substrate binding. Antibodies can be prepared against specific fragments containing sites required for function or against intact PGP synthase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. Nos. 5,625, 126; 5,633,425; 5,569,825; 5,661,016; and 5,545,806.

The invention also encompasses kits for using antibodies to detect the presence of an PGP synthase protein in a biological sample. The kit can comprise antibodies such as a labeled or labelable antibody and a compound or agent for detecting PGP synthase in a biological sample; means for determining the amount of PGP synthase in the sample; and means for comparing the amount of PGP synthase in the sample with a standard. The compound or agent can be packaged in a suitable container. The kit can further comprise instructions for using the kit to detect PGP synthase.

Polynucleotides

The nucleotide sequence in SEQ ID NO:1 was obtained by sequencing the deposited human cDNA. Accordingly, the sequence of the deposited clones are controlling as to any discrepancies between the two and any reference to the sequences of SEQ ID NO:1, includes reference to the sequences of the deposited cDNA.

The specifically disclosed cDNAs comprise the coding region and 5' and 3' untranslated sequences in SEQ ID NO:1.

The invention provides isolated polynucleotides encoding the novel PGP synthase. The term "PGP synthase polynucleotide" or "PGP synthase nucleic acid" refers to the sequences shown in SEQ ID NO:1, SEQ ID NO:3, or in the deposited cDNAs. The term "PGP synthase polynucleotide" or "PGP synthase nucleic acid" further includes variants and fragments of the PGP synthase polynucleotides. Generally, nucleic acid molecules that are fragments of the 27411 nucleic acid comprise at least 15, 20, 38, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1400, 1500, 1600, 1700, 1800, 1900, 2000, 2100, 2200, 2300, 2400, 2500, 2600, 2686 nucleotides or up to the number of nucleotides present in a full-length human PGP synthase-like nucleotide sequence disclosed herein (for example, 2686 nucleotides for SEQ ID NO:1) depending upon the intended use. Alternatively, a nucleic acid molecule that is a fragment of a 27411-like nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1800, 1800–1900, 1900–2000, 2000–2100, 2100–2200, 2200–2300, 2300–2400, 2400–2500, 2500–2600, 2600–2686 of SEQ ID NO:1.

An "isolated" PGP synthase nucleic acid is one that is separated from other nucleic acid present in the natural source of the PGP synthase nucleic acid. Preferably, an "isolated" nucleic acid is free of sequences which naturally flank the PGP synthase nucleic acid (i.e., sequences located at the 5' and 3' ends of the nucleic acid) in the genomic DNA of the organism from which the nucleic acid is derived. However, there can be some flanking nucleotide sequences, for example up to about 5 kb. The important point is that the PGP synthase nucleic acid is isolated from flanking sequences such that it can be subjected to the specific manipulations described herein, such as recombinant expression, preparation of probes and primers, and other uses specific to the PGP synthase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The PGP synthase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The PGP synthase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

PGP synthase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

PGP synthase nucleic acid can comprise the nucleotide sequences shown in SEQ ID NO:1 and SEQ ID NO:3 corresponding to human PGP synthase cDNA.

In one embodiment, the PGP synthase nucleic acid comprises only the coding region.

The invention further provides variant PGP synthase polynucleotides, and fragments thereof, that differ from the nucleotide sequences shown in SEQ ID NO:1 due to degeneracy of the genetic code and thus encode the same protein as that encoded by the nucleotide sequences shown in SEQ ID NO:1 or SEQ ID NO:3.

The invention also provides PGP synthase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Generally, nucleotide sequences variants of the invention will have at least 60%, 65%, 70%, 75%, 80%, 85%, 90%, 91%, 92%, 93%, 94%, 95%, 96%, 97%, 98%, or 99% identity to the nucleotide sequence disclosed herein. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a PGP synthase that is at least about 60–65%, 65–70%, typically at least about 70–75%, more typically at least about 80–85%, and most typically at least about 90–95% or more homologous to the nucleotide sequence shown in SEQ ID NO:1, SEQ ID NO:3 or a fragment of these sequences. Such nucleic acid molecules can readily be identified as being able to hybridize under stringent conditions, to the nucleotide sequence shown in SEQ ID NO:1, SEQ ID NO:3, or a fragment of these sequences. It is understood that stringent hybridization does not indicate substantial homology where it is due to general homology, such as poly A sequences, or sequences common to all or most proteins, all PGP synthase, all phospho group transferases. Moreover, it is understood that variants do not include any of the nucleic acid sequences that may have been disclosed prior to the invention.

As used herein, the term "hybridizes under stringent conditions" describes conditions for hybridization and washing. Stringent conditions are known to those skilled in the art and can be found in *Current Protocols in Molecular Biology* John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally occurring nucleic acid molecule.

As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:1, SEQ ID NO:3 or the complement thereof. In one embodiment, the nucleic acid consists of a portion of the nucleotide sequence of SEQ ID NO:1, SEQ ID NO:3 or the complement thereof.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, preferably at least about 15, 18, 20, 23 or 25 nucleotides, and can be 30, 40, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600 or more nucleotides in length. Longer fragments, for example, 30 or more nucleotides in length, which encode antigenic proteins or polypeptides described herein are useful.

For PGP synthase, for example, nucleotide sequences from about 1 to about 285, from about 1992 to about 2041 and from about 2562 to about 2643 are especially relevant and encompass fragments of 5–10, 10–15, 15–20, 20–25, etc., as disclosed herein. The nucleotide sequence from about 1 to about 1991 encompasses fragments greater than about 315, 325, 345, 355 or 365 nucleotides; the nucleotide sequence from about 1074 to about 2689 encompasses fragments greater than 167, 175, 185, 195, or 205 nucleotides; and the nucleotide sequence from about 2507 to about 2689 encompasses fragments greater than 28, 35, 40, 45, 50, or 55 nucleotides.

The fragment can be single or double-stranded and can comprise DNA or RNA. The fragment can be derived from either the coding or the non-coding sequence.

In another embodiment an isolated PGP synthase nucleic acid encodes the entire coding region. In another embodiment the isolated PGP synthase nucleic acid encodes a sequence corresponding to the mature protein. For example, the mature form of the PGP synthase is from about amino acid 68 to the last amino acid. Other fragments include nucleotide sequences encoding the amino acid fragments described herein.

Thus, PGP synthase nucleic acid fragments further include sequences corresponding to the domains described herein, subregions also described, and specific functional sites. PGP synthase nucleic acid fragments also include combinations of the domains, segments, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a PGP synthase fragment includes any nucleic acid sequence that does not include the entire gene.

The invention also provides PGP synthase nucleic acid fragments that encode epitope bearing regions of the PGP synthase proteins described herein.

Nucleic acid fragments, according to the present invention, are not to be construed as encompassing those fragments that may have been disclosed prior to the invention.

Polynucleotide Uses

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO:1 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The PGP synthase polynucleotides are thus useful for probes, primers, and in biological assays.

Where the polynucleotides are used to assess PGP synthase properties or functions, such as in the assays described herein, all or less than all of the entire cDNA can be useful. Assays specifically directed to PGP synthase functions, such as assessing agonist or antagonist activity, encompass the use of known fragments. Further, diagnostic methods for assessing PGP synthase function can also be practiced with any fragment, including those fragments that may have been known prior to the invention. Similarly, in methods involving treatment of PGP synthase dysfunction, all fragments are encompassed including those, which may have been known in the art.

The PGP synthase polynucleotides are useful as a hybridization probe for cDNA and genomic DNA to isolate a full-length cDNA and genomic clones encoding the polypeptides described in SEQ ID NO:2 and to isolate cDNA and genomic clones that correspond to variants producing the same polypeptides shown in SEQ ID NO:2 or the other variants described herein. Variants can be isolated from the same tissue and organism from which the polypeptides shown in SEQ ID NO:2 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the PGP synthase. Accordingly, it could be derived from 5' noncoding regions, the coding region, and 3' noncoding regions.

The nucleic acid probe can be, for example, the full-length cDNA of SEQ ID NO:1 or a fragment thereof, such as an oligonucleotide of at least 10–15, 15–20, 20–25, 25–30, 100, 250, or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO:1 or SEQ ID NO:3 and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uraci (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioocganic Med. Chem. Lett.* 5:1119.

The nucleic acid molecules and fragments of the invention can also include other appended groups such as peptides (e.g., for targeting host cell PGP synthase in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The PGP synthase polynucleotides are also useful as primers for PCR to amplify any given region of a PGP synthase polynucleotide.

The PGP synthase polynucleotides are also useful for constructing recombinant vectors. Such vectors include expression vectors that express a portion of, or all of, the PGP synthase polypeptides. Vectors also include insertion vectors, used to integrate into another polynucleotide sequence, such as into the cellular genome, to alter in situ expression of PGP synthase genes and gene products. For example, an endogenous PGP synthase coding sequence can be replaced via homologous recombination with all or part of the coding region containing one or more specifically introduced mutations.

The PGP synthase polynucleotides are also useful for expressing antigenic portions of the PGP synthase proteins.

The PGP synthase polynucleotides are also useful as probes for determining the chromosomal positions of the PGP synthase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man,* available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The PGP synthase polynucleotide probes are also useful to determine patterns of the presence of the gene encoding the PGP synthase and their variants with respect to tissue distribution, for example, whether gene duplication has occurred and whether the duplication occurs in all or only a subset of tissues. The genes can be naturally occurring or can have been introduced into a cell, tissue, or organism exogenously.

The PGP synthase polynucleotides are also useful for designing ribozymes corresponding to all, or a part, of the mRNA produced from genes encoding the polynucleotides described herein.

The PGP synthase polynucleotides are also useful for constructing host cells expressing a part, or all, of the PGP synthase polynucleotides and polypeptides.

The PGP synthase polynucleotides are also useful for constructing transgenic animals expressing all, or a part, of the PGP synthase polynucleotides and polypeptides.

The PGP synthase polynucleotides are also useful for making vectors that express part, or all, of the PGP synthase polypeptides.

The PGP synthase polynucleotides are also useful as hybridization probes for determining the level of PGP synthase nucleic acid expression. Accordingly, the probes can be used to detect the presence of, or to determine levels of, PGP synthase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the PGP synthase genes.

Alternatively, the probe can be used in an in situ hybridization context to assess the position of extra copies of the PGP synthase genes, as on extrachromosomal elements or as integrated into chromosomes in which the PGP synthase gene is not normally found, for example as a homogeneously staining region.

These uses are relevant for diagnosis of disorders involving an increase or decrease in PGP synthase expression relative to normal, such as a proliferative disorder or a differentiative or developmental disorder.

Disorders in which PGP synthase expression is relevant include, but are not limited to disease conditions associated with defective cardiolipin (CL) and phosphatidylglycerol (PG) biosynthesis and metabolism.

Tissues and/or cells in which 27411 is expressed are described above herein. As such, the gene is particularly relevant for the treatment of disorders involving these tissues.

Furthermore, disorders in which 27411 expression is relevant are disclosed herein above.

Thus, the present invention provides a method for identifying a disease or disorder associated with aberrant expression or activity of PGP synthase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the PGP synthase, such as by measuring the level of a PGP synthase-encoding nucleic acid in a sample of cells from a subject e.g., mRNA or genomic DNA, or determining if the PGP synthase gene has been mutated.

Nucleic acid expression assays are useful for drug screening to identify compounds that modulate PGP synthase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the PGP synthase gene. The method typically includes assaying the ability of the compound to modulate the expression of the PGP synthase nucleic acid and thus identifying a compound that can be used to treat a disorder characterized by undesired PGP synthase nucleic acid expression.

The assays can be performed in cell-based and cell-free systems. Cell-based assays include cells naturally expressing the PGP synthase nucleic acid or recombinant cells genetically engineered to express specific nucleic acid sequences, for example those cited above and in the background.

Alternatively, candidate compounds can be assayed in vivo in patients or in transgenic animals.

The assay for PGP synthase nucleic acid expression can involve direct assay of nucleic acid levels, such as mRNA levels, or on collateral compounds involved in the PGP synthase catalyzed reaction. Further, the expression of genes that are up- or down-regulated in response to the PGP synthase signal pathway can also be assayed. In this embodiment the regulatory regions of these genes can be operably linked to a reporter gene such as luciferase.

Thus, modulators of PGP synthase gene expression can be identified in a method wherein a cell is contacted with a candidate compound and the expression of mRNA determined. The level of expression of PGP synthase mRNA in the presence of the candidate compound is compared to the level of expression of PGP synthase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate PGP synthase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid. Disorders that the gene is particularly relevant for treating have been disclosed herein above.

Alternatively, a modulator for PGP synthase nucleic acid expression can be a small molecule or drug identified using the screening assays described herein as long as the drug or small molecule inhibits the PGP synthase nucleic acid expression.

The PGP synthase polynucleotides are also useful for monitoring the effectiveness of modulating compounds on the expression or activity of the PGP synthase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The PGP synthase polynucleotides are also useful in diagnostic assays for qualitative changes in PGP synthase nucleic acid, and particularly in qualitative changes that lead to pathology. The polynucleotides can be used to detect mutations in PGP synthase genes and gene expression products such as mRNA. The polynucleotides can be used as hybridization probes to detect naturally-occurring genetic mutations in the PGP synthase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the PGP synthase gene associated with a dysfunction provides a diagnostic tool for an active disease or susceptibility to disease when the disease results from overexpression, underexpression, or altered expression of a PGP synthase.

Mutations in the PGP synthase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an PGP synthase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant PGP synthase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The PGP synthase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the PGP synthase gene that results in altered affinity for a coenzyme could result in an excessive or decreased drug effect with standard concentrations of the coenzyme that activate the PGP synthase. Accordingly, the PGP synthase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The PGP synthase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The PGP synthase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the PGP synthase sequence can be used to provide an alternative technique, which determines the actual DNA sequence of selected fragments in the genome of an individual. Thus, the PGP synthase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The PGP synthase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The PGP synthase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The PGP synthase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The PGP synthase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of PGP synthase probes can be used to identify tissue by species and/or by organ type.

In a similar fashion, these primers and probes can be used to screen tissue culture for contamination (i.e. screen for the presence of a mixture of different types of cells in a culture).

Alternatively, the PGP synthase polynucleotides can be used directly to block transcription or translation of PGP synthase gene sequences by means of antisense or ribozyme constructs. Thus, in a disorder characterized by abnormally high or undesirable PGP synthase gene expression, nucleic acids can be directly used for treatment.

The PGP synthase polynucleotides are thus useful as antisense constructs to control PGP synthase gene expression in cells, tissues, and organisms. A DNA antisense polynucleotide is designed to be complementary to a region of the gene involved in transcription, preventing transcription and hence production of PGP synthase protein. An antisense RNA or DNA polynucleotide would hybridize to the mRNA and thus block translation of mRNA into PGP synthase protein.

Examples of antisense molecules useful to inhibit nucleic acid expression include antisense molecules complementary to a fragment of the 5' untranslated region of SEQ ID NO:1, which also includes the start codon and antisense molecules which are complementary to a fragment of the 3' untranslated region of SEQ ID NO:1.

Alternatively, a class of antisense molecules can be used to inactivate mRNA in order to decrease expression of a PGP synthase nucleic acid. Accordingly, these molecules can treat a disorder characterized by abnormal or undesired PGP synthase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the PGP synthase protein.

The PGP synthase polynucleotides also provide vectors for gene therapy in patients containing cells that are aberrant in PGP synthase gene expression. Thus, recombinant cells, which include the patient's cells that have been engineered ex vivo and returned to the patient, are introduced into an individual where the cells produce the desired PGP synthase protein to treat the individual.

The invention also encompasses kits for detecting the presence of an PGP synthase nucleic acid in a biological sample. For example, the kit can comprise reagents such as a labeled or labelable nucleic acid or agent capable of detecting PGP synthase nucleic acid in a biological sample; means for determining the amount of PGP synthase nucleic acid in the sample; and means for comparing the amount of PGP synthase nucleic acid in the sample with a standard. The compound or agent can be packaged in a suitable container. The kit can further comprise instructions for using the kit to detect PGP synthase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the PGP synthase polynucleotides. The term "vector" refers to a vehicle, preferably a nucleic acid molecule that can transport the PGP synthase polynucleotides. When the vector is a nucleic acid molecule, the PGP synthase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the PGP synthase polynucleotides. Alternatively, the vector may integrate into the host cell genome and produce additional copies of the PGP synthase polynucleotides when the host cell replicates.

The invention provides vectors for the maintenance (cloning vectors) or vectors for expression (expression vectors) of the PGP synthase polynucleotides. The vectors can function in procaryotic or eukaryotic cells or in both (shuttle vectors).

Expression vectors contain cis-acting regulatory regions that are operably linked in the vector to the PGP synthase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the PGP synthase polynucleotides from the vector. Alternatively, a trans-acting factor may be supplied by the host cell. Finally, a trans-acting factor can be produced from the vector itself.

It is understood, however, that in some embodiments, transcription and/or translation of the PGP synthase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

A variety of expression vectors can be used to express a PGP synthase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The PGP synthase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the polypeptide as a fusion protein. Accordingly, the invention provides fusion vectors that allow for the production of the PGP synthase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11 d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The PGP synthase polynucleotides can also be expressed by expression vectors that are operative in yeast. Examples of vectors for expression in yeast e.g., *S. cerevisiae* include pYepSec1 (Baldari et al. (1987) *EMBO J.* 6:229–234 ), pMFa (Kuijan et al. (1982) *Cell* 30:933–943), pJRY88 (Schultz et al. (1987) *Gene* 54:113–123), and pYES2 (Invitrogen Corporation, San Diego, Calif.).

The PGP synthase polynucleotides can also be expressed in insect cells using, for example, baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow et al. (1989) *Virology* 170: 31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the PGP synthase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed.,* Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the PGP synthase polynucleotides can be introduced either alone or with other polynucleotides that are not related to the PGP synthase polynucleotides such as those providing trans-acting factors for expression vectors. When more than one vector is introduced into a cell, the vectors can be introduced independently, co-introduced or joined to the PGP synthase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the PGP synthase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

The host cells expressing the polypeptides described herein, and particularly recombinant host cells, have a variety of uses. First, the cells are useful for producing PGP synthase proteins or polypeptides that can be further purified to produce desired amounts of PGP synthase protein or fragments. Thus, host cells containing expression vectors are useful for polypeptide production.

Host cells are also useful for conducting cell-based assays involving the PGP synthase or PGP synthase fragments. Thus, a recombinant host cell expressing a native PGP synthase is useful to assay for compounds that stimulate or inhibit PGP synthase function. These include, but are not limited to those disclosed herein and above in the background.

Host cells are also useful for identifying PGP synthase mutants in which these functions are affected. If the mutants naturally occur and give rise to a pathology, host cells containing the mutations are useful to assay compounds that have a desired effect on the mutant PGP synthase (for example, stimulating or inhibiting function) which may not be indicated by their effect on the native PGP synthase.

Recombinant host cells are also useful for expressing the chimeric polypeptides described herein to assess compounds that activate or suppress activation by means of a heterologous domain, segment, site, and the like, as disclosed herein.

Further, mutant PGP synthase can be designed in which one or more of the various functions is engineered to be increased or decreased and used to augment or replace PGP synthase proteins in an individual. Thus, host cells can provide a therapeutic benefit by replacing an aberrant PGP synthase or providing an aberrant PGP synthase that provides a therapeutic result. In one embodiment, the cells provide PGP synthase that are abnormally active.

In another embodiment, the cells provide PGP synthase that are abnormally inactive. These PGP synthase can compete with endogenous PGP synthase in the individual.

In another embodiment, cells expressing PGP synthase that are not catalytically active, are introduced into an individual in order to compete with endogenous PGP synthase. For example, in the case in which excessive amounts of a PGP synthase substrate or effector is part of a treatment modality, it may be necessary to inactivate this molecule at a specific point in treatment. Providing cells that compete for the molecule, but which cannot be affected by PGP synthase activation would be beneficial.

Homologously recombinant host cells can also be produced that allow the in situ alteration of endogenous PGP synthase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the PGP synthase polynucleotides or sequences proximal or distal to an PGP synthase gene are allowed to integrate into a host cell genome by homologous recombination where expression of the gene can be affected. In one embodiment, regulatory sequences are introduced that either increase or decrease expression of an endogenous sequence. Accordingly, a PGP synthase protein can be produced in a cell not normally producing it. Alternatively, increased expression of PGP synthase protein can be effected in a cell normally producing the protein at a specific level. Further, expression can be decreased or eliminated by introducing a specific regulatory sequence. The regulatory sequence can be heterologous to the PGP synthase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant PGP synthase proteins. Such mutations could be introduced, for example, into the specific functional regions such as the ligand-binding site.

In one embodiment, the host cell can be a fertilized oocyte or embryonic stem cell that can be used to produce a transgenic animal containing the altered PGP synthase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous PGP synthase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a PGP synthase protein and identifying and evaluating modulators of PGP synthase protein activity.

Other examples of transgenic animals include non-human primates, sheep, dogs, cows, goats, chickens, and amphibians.

In one embodiment, a host cell is a fertilized oocyte or an embryonic stem cell into which PGP synthase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the PGP synthase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the PGP synthase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the crelloxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect substrate binding may not be evident from in vitro cell-free or cell-based assays. Accordingly, it is useful to provide non-human transgenic animals to assay in vivo PGP synthase function, including substrate, cofactor and substituted phospho group transfer interactions. Similar methods could be used to determine the effect of specific mutant PGP synthase and the effect of chimeric PGP synthase on such enzyme functions. It is also possible to assess the effect of null mutations, that is mutations that substantially or completely eliminate one or more PGP synthase functions.

In general, methods for producing transgenic animals include introducing a nucleic acid sequence according to the present invention, the nucleic acid sequence capable of expressing the PGP synthase protein in a transgenic animal, into a cell in culture or in vivo. When introduced in vivo, the nucleic acid is introduced into an intact organism such that one or more cell types and, accordingly, one or more tissue types, express the nucleic acid encoding the PGP synthase protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The PGP synthase nucleic acid molecules, polypeptides and modulators of the polypeptide and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PGP synthase protein or anti-PGP synthase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by; for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

OTHER EMBODIMENTS

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 27411 preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 27411 nucleic acid, polypeptide, or antibody.

The capture probes can be a set of nucleic acids from a selected sample, e.g., a sample of nucleic acids derived from a control or non-stimulated tissue or cell.

The method can include contacting the 27411 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes with an allele of 27411. Such methods can be used to diagnose a subject, e.g., to evaluate risk for a disease or disorder, to evaluate suitability of a selected treatment for a subject, to evaluate whether a subject has a disease or disorder. 27411 is associated with PGP synthase activity, thus it is useful for disorders associated with abnormal PGP synthase activity, cardiolipin biosynthesis, and PG biosynthesis.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express 27411 or from a cell or subject in which a 27411 mediated response has been elicited, e.g., by contact of the cell with 27411 nucleic acid or protein, or administration to the cell or subject 27411 nucleic acid or protein; contacting the array with one or more inquiry probe, wherein an inquiry probe can be a nucleic acid, polypeptide, or antibody (which is preferably other than 27411 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 27411 (or does not express as highly as in the case of the 27411 positive plurality of capture probes) or from a cell or subject which in which a 27411 mediated response has not been elicited (or has been elicited to a lesser extent than in the first sample); contacting the array with one or more inquiry probes (which is preferably other than a 27411 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 27411, e.g., analyzing structure, function, or relatedness to other nucleic acid or amino acid sequences. The method includes: providing a 27411 nucleic acid or amino acid sequence; comparing the 27411 sequence with one or more preferably a plurality of sequences from a collection of sequences, e.g., a nucleic acid or protein sequence database; to thereby analyze 27411.

Preferred databases include GenBank™. The method can include evaluating the sequence identity between a 27411 sequence and a database sequence. The method can be performed by accessing the database at a second site, e.g., over the internet.

In another aspect, the invention features, a set of oligonucleotides, useful, e.g., for identifying SNP's, or identifying specific alleles of 27411. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide that hybridizes to a second allele.

This invention is further illustrated by the following examples that should not be construed as limiting. The contents of all references, patents and published patent applications cited throughout this application are incorporated herein by reference.

EXPERIMENTAL

EXAMPLE 1

Identification and Characterization of 27411, Human PGP Synthase

The human 27411 sequence (FIG. 1; SEQ ID NO:1), that is approximately 2686 nucleotides long including untranslated regions, contains a predicted methionine-initiated coding sequence of about 1671 nucleotides (nucleotides 315–1985 of SEQ ID NO:1; SEQ ID NO:3). The coding sequence encodes a 556 amino acid protein (SEQ ID NO:2).

PFAM analysis indicates that the 27411 polypeptide shares a high degree of sequence similarity with phospholipase D domains from amino acids 215–241 and 460–493 of SEQ ID NO:2. The phospholipase D domain (HMM) has been assigned the PFAM Accession PF00614 (see pfam.wustl.edu/). For general information regarding PFAM identifiers, PS prefix and PF prefix domain identification numbers, refer to Sonnhammer et al. (1997) *Protein* 28:405–420 and www.psc.edu/general/software/packages/pfam/pfam.html.

In one embodiment, a 27411-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 26, or 27 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, pfam.wustl.edu/cgi-bin/getdesc?name=7tm-1, and Zagotta W. N. et al. (1996) *Annual Rev. Neuronsci.* 19:235–63, the contents of which are incorporated herein by reference.

In a preferred embodiment, a 27411-like polypeptide or protein has at least one transmembrane domain or a region which includes at least 18, 20, 22, 24, 25, 26, or 27 amino acid residues and has at least about 60%, 70% 80% 90% 95%, 99%, or 100% sequence identity with a "transmembrane domain," e.g., at least one transmembrane domain of human 27411-like (e.g., amino acid residues 51 to 73 or 469 to 485 of SEQ ID NO:2).

In another embodiment, a 27411-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 27411-like, or 27411-like protein.

In a preferred embodiment, a 27411-like polypeptide or protein has a "non-transmembrane domain" or a region which includes at least about 1–396, preferably about 100–396, more preferably about 200–350, and even more preferably about 240–280 amino acid residues, and has at least about 60%, 70% 80% 90% 95%, 99% or 100% sequence identity with a "non-transmembrane domain", e.g., a non-transmembrane domain of human 27411-like (e.g., residues 1 to 51, 74 to 468, and 486 to 556 of SEQ ID NO:2). Preferably, a non-transmembrane domain is capable of catalytic activity (e.g., PGP synthase).

A non-transmembrane domain located at the N-terminus of a 27411-like protein or polypeptide is referred to herein as an "N-terminal non-transmembrane domain." As used herein, an "N-terminal non-transmembrane domain" includes an amino acid sequence having about 1–51, preferably about 10–45, more preferably about 20–40, or even more preferably about 20–35 amino acid residues in length and is located outside the boundaries of a membrane. For example, an N-terminal non-transmembrane domain is located at about amino acid residues 1 to 50 of SEQ ID NO:2.

Similarly, a non-transmembrane domain located at the C-terminus of 27411-like protein or polypeptide is referred to herein as a "C-terminal non-transmembrane domain." As used herein, an "C-terminal non-transmembrane domain" includes an amino acid sequence having about 1–71, preferably about 10–75, preferably about 20–60, more preferably about 25–45 amino acid residues in length and is located outside the boundaries of a membrane. For example, an C-terminal non-transmembrane domain is located at about amino acid residues 486 to 556 of SEQ ID NO:2.

A 27411-like molecule can further include a signal sequence. As used herein, a "signal sequence" refers to a peptide of about 20–80 amino acid residues in length which occurs at the N-terminus of secretory and integral membrane proteins and which contains a majority of hydrophobic amino acid residues. For example, a signal sequence contains at least about 12–25 amino acid residues, preferably about 30–70 amino acid residues, more preferably about 68 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 27411-like protein contains a signal sequence of about amino acids 1 to 68 of SEQ ID NO:2. The "signal sequence" may be cleaved during processing of the mature protein. The mature 27411-like protein corresponds to amino acids 69 to 556 of SEQ ID NO:2.

The 27411 protein displays approximately 26% identity from aa 85–522 to a ProDom consensus sequence found in O-phosphatidyltransferase CDP-diacylglycerol serine phosphatidylserine synthase transferase phospholipid biosynthesis; approximately 31% identity from aa 476–554 to a ProDom consensus sequence found in receptor nuclear co-repressor N-cor retinoid X interacting protein; approximately 31% identity from aa 260–324 to a ProDom consensus sequence found in SIP1 protein phosphorylation; and, approximately 38% identity from aa 210–247 to a ProDom consensus sequence found in protein transferase HP019 transmembrane CSGC-MDOG intergenic region. These sequences were identified by the ProDom program, which is available from INRA, GREG (107/94), MESR (ACC-SV13), the CNRS "Genome Initiative" and the European Union. The ProDom Program (see www.toulouse.inra.fr/prodom.html) allows analysis of domain arrangements in proteins and protein families. A detailed description of ProDom analysis can be found in Corpet et al. (1999) *Nuc. Acids Res.* 27:263–267.

EXAMPLE 2

Tissue Distribution of 27411 mRNA

Expression levels of 27411 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions. The results of the Taqman® analysis are shown in FIG. 5.

TaqMan analysis of 27411 revealed expression in a number of tissues, including the following: artery, diseased artery, vein, coronary smooth muscle cells, HUVEC (umbilical vein endothelial cells), hemangioma, heart, congestive heart failure heart, kidney, skeletal muscle, adipose, pancreas, primary osteoblasts, differentiated osteoclasts, skin, spinal cord, brain cortex, brain hypothalamus, nerve, dorsal root ganglion, breast, breast tumor, ovary, ovarian tumor, prostate, prostate tumor, salivary glands, colon, colon tumor, lung, lung tumor, chronic obstructive pulmonary disease lung, inflammatory bowel disease colon, liver, liver fibrosis, spleen, tonsil, lymph node, small intestine, macrophages, synovium, mononuclear bone marrow cells, activated peripheral blood mononuclear cells, neutrophils, megakaryocytes, and erythroid tissue.

Northern blot hybridizations with various RNA samples are performed under standard conditions and washed under stringent conditions, i.e., 0.2×SSC at 65° C. A DNA probe corresponding to all or a portion of the 27411 cDNA (SEQ ID NO:1) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

EXAMPLE 3

Recombinant Expression of 27411 in Bacterial Cells

In this example, 27411 is expressed as a recombinant glutathione-S-transferase (GST) fusion polypeptide in *E. coli* and the fusion polypeptide is isolated and characterized. Specifically, 27411 is fused to GST and this fusion polypeptide is expressed in *E. coli*, e.g., strain PEB 199. Expression of the GST-27411 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

EXAMPLE 4

Expression of Recombinant 27411 Protein in COS Cells

To express the 27411 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 27411 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 27411 DNA sequence is amplified by PCR using two primers. The 5' primer contains the restriction site of interest followed by approximately twenty nucleotides of the 27411 coding sequence starting from the initiation codon; the 3' end sequence contains complementary sequences to the other restriction site of interest, a translation stop codon, the HA tag or FLAG tag and the last 20 nucleotides of the 27411 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 27411 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 27411-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989. The expression of the 27411 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 27411 coding sequence is cloned directly into the polylinker of the pcDNA/Amp vector using the appropriate restriction sites. The resulting plasmid is transfected into COS cells in the manner described above, and the expression of the 27411 polypeptide is detected by radiolabelling and immunoprecipitation using a 27411 specific monoclonal antibody.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

SEQUENCE LISTING

```
<160> NUMBER OF SEQ ID NOS: 3

<210> SEQ ID NO 1
<211> LENGTH: 2686
<212> TYPE: DNA
<213> ORGANISM: Homo sapiens
<220> FEATURE:
<221> NAME/KEY: CDS
<222> LOCATION: (315)...(1985)
<220> FEATURE:
<221> NAME/KEY: misc_feature
<222> LOCATION: (1)...(2686)
<223> OTHER INFORMATION: n = A,T,C or G

<400> SEQUENCE: 1
atccacgctt ttgcntgacc cttgcttggt tcaacttana ggtctttgtt tcggttttct      60
tgttnngcnc cggttacaga tccaaagttt tgaaaaaacc anaaaagtna nctggtaagt     120
taagtctttt ttgtcttttta tttccagntc cnggaatccg ggtggttggt gcaaantcaa    180
aaganttgtt cctcaagtga atgttgcntt tacttcttag gcntgtacgg aaagtgttat    240
ttttgtttta aaagctggga attcttanta cgacttcact ataggagtc gacccacgcg     300 tccggcgagt ctcc atg gcg gtg gcg gcg gca gct gcg gcg gga ccc gtg       350
              Met Ala Val Ala Ala Ala Ala Ala Ala Gly Pro Val
                1               5                  10 ttc tgg agg cga ctg ctg ggc ctc ctg cct ggc cgc cca ggg ctg gcc       398
Phe Trp Arg Arg Leu Leu Gly Leu Leu Pro Gly Arg Pro Gly Leu Ala
        15                  20                  25 gcg ctc ctg gga cgc ctg tcc gac cgc ctc ggc agg aac cgg gac cgc       446
Ala Leu Leu Gly Arg Leu Ser Asp Arg Leu Gly Arg Asn Arg Asp Arg
    30                  35                  40 cag cgc agg agg tca cca tgg ctg tta ttg gct ccc ttg ctg tcc cca       494
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Gln   | Arg   | Arg   | Arg   | Ser   | Pro   | Trp   | Leu   | Leu   | Leu   | Ala   | Pro   | Leu   | Leu   | Ser   | Pro   |      |
| 45    |       |       |       |       | 50    |       |       |       |       | 55    |       |       |       |       | 60    |      |

```
gct gtt ccc cag gtc acc tcc cca cct tgc tgc ctg tgt cca gaa ggc        542
Ala Val Pro Gln Val Thr Ser Pro Pro Cys Cys Leu Cys Pro Glu Gly
                65                  70                  75 gtg cac cgg ttc cag tgg atc aga aac ctg gtt cca gaa ttt gga gtc        590
Val His Arg Phe Gln Trp Ile Arg Asn Leu Val Pro Glu Phe Gly Val
            80                  85                  90 tcc agt tct cac gtt agg gtg ctt tct tcc ccg gca gag ttt ttc gag        638
Ser Ser Ser His Val Arg Val Leu Ser Ser Pro Ala Glu Phe Phe Glu
        95                 100                 105 ctc atg aag ggg cag ata aga gta gcc aag agg cgg gtc gtg atg gca        686
Leu Met Lys Gly Gln Ile Arg Val Ala Lys Arg Arg Val Val Met Ala
    110                 115                 120 tcc ctc tac ctg ggg aca ggt cct ttg gaa cag gag ctg gtg gac tgc        734
Ser Leu Tyr Leu Gly Thr Gly Pro Leu Glu Gln Glu Leu Val Asp Cys
125                 130                 135                 140 ctg gaa agt act cta gaa aag tca ctc caa gca aag ttt cct tca aat        782
Leu Glu Ser Thr Leu Glu Lys Ser Leu Gln Ala Lys Phe Pro Ser Asn
                145                 150                 155 ctc aag gtc tcc att ctc tta gac ttc acg cgg ggc tca cga ggt cgg        830
Leu Lys Val Ser Ile Leu Leu Asp Phe Thr Arg Gly Ser Arg Gly Arg
            160                 165                 170 aag aac tcc cgc aca atg ctg ctc cca ctc ctg cgg agg ttc cca gag        878
Lys Asn Ser Arg Thr Met Leu Leu Pro Leu Leu Arg Arg Phe Pro Glu
        175                 180                 185 cag gtc cga gtc tcc ctc ttt cac acg ccg cac ctc cgt ggg ctg ctt        926
Gln Val Arg Val Ser Leu Phe His Thr Pro His Leu Arg Gly Leu Leu
    190                 195                 200 cgg ctc ctc atc cct gag cgc ttc aac gag acc atc ggc ctc cag cac        974
Arg Leu Leu Ile Pro Glu Arg Phe Asn Glu Thr Ile Gly Leu Gln His
205                 210                 215                 220 att aag gtg tac ctc ttc gac aac agc gtc atc ttg agc ggt gca aac       1022
Ile Lys Val Tyr Leu Phe Asp Asn Ser Val Ile Leu Ser Gly Ala Asn
                225                 230                 235 ctg agt gac tcc tac ttc acc aac cgc cag gac cgc tac gtg ttc ctg       1070
Leu Ser Asp Ser Tyr Phe Thr Asn Arg Gln Asp Arg Tyr Val Phe Leu
            240                 245                 250 cag gac tgt gcg gag att gcc gac ttc ttc acg gag ctg gtg gac gcg       1118
Gln Asp Cys Ala Glu Ile Ala Asp Phe Phe Thr Glu Leu Val Asp Ala
        255                 260                 265 gtg ggg gat gtg tcc ctg cag ctg cag ggg gac gac acg gtg cag gtg       1166
Val Gly Asp Val Ser Leu Gln Leu Gln Gly Asp Asp Thr Val Gln Val
    270                 275                 280 gtg gat ggg atg gtg cat cct tac aaa ggg gac cgg gcc gag tac tgc       1214
Val Asp Gly Met Val His Pro Tyr Lys Gly Asp Arg Ala Glu Tyr Cys
285                 290                 295                 300 aag gca gcc aat aag agg gtc atg gat gtg atc aac tca gcc agg acc       1262
Lys Ala Ala Asn Lys Arg Val Met Asp Val Ile Asn Ser Ala Arg Thr
                305                 310                 315 cgc cag cag atg ctg cat gcc cag acc ttc cac agc aac tct ctt ttg       1310
Arg Gln Gln Met Leu His Ala Gln Thr Phe His Ser Asn Ser Leu Leu
            320                 325                 330 acc cag gaa gat gca gca gct gct ggg gat cgc aga cca gcc cct gac       1358
Thr Gln Glu Asp Ala Ala Ala Ala Gly Asp Arg Arg Pro Ala Pro Asp
        335                 340                 345 acc tgg att tat ccg ctg att cag atg aag ccc ttc gag att caa atc       1406
Thr Trp Ile Tyr Pro Leu Ile Gln Met Lys Pro Phe Glu Ile Gln Ile
    350                 355                 360
```

```
gat gag att gtc act gag acc ctg ttg act gag gcg gag cgc ggg gca    1454
Asp Glu Ile Val Thr Glu Thr Leu Leu Thr Glu Ala Glu Arg Gly Ala
365                 370                 375                 380 aag gtc tac ctc acc act ggc tat ttc aac ctg acc cag gcc tac atg    1502
Lys Val Tyr Leu Thr Thr Gly Tyr Phe Asn Leu Thr Gln Ala Tyr Met
            385                 390                 395 gac ctg gtc ttg ggc act cgg gct gag tac cag atc ctg ctg gcc tca    1550
Asp Leu Val Leu Gly Thr Arg Ala Glu Tyr Gln Ile Leu Leu Ala Ser
        400                 405                 410 cca gag gtg aat ggc ttc ttt ggg gcc aag ggg gtg gcc ggc gcc atc    1598
Pro Glu Val Asn Gly Phe Phe Gly Ala Lys Gly Val Ala Gly Ala Ile
    415                 420                 425 cca gcg gcc tat gtg cac atc gag cga cag ttc ttc agt gag gtg tgc    1646
Pro Ala Ala Tyr Val His Ile Glu Arg Gln Phe Phe Ser Glu Val Cys
430                 435                 440 agc ctg gga cag cag gag cgg gtc cag ctt cag gag tac tgg cgg agg    1694
Ser Leu Gly Gln Gln Glu Arg Val Gln Leu Gln Glu Tyr Trp Arg Arg
445                 450                 455                 460 ggc tgg acg ttc cac gcc aaa ggc ctc tgg ctg tac ctg gca ggg agc    1742
Gly Trp Thr Phe His Ala Lys Gly Leu Trp Leu Tyr Leu Ala Gly Ser
            465                 470                 475 agc ctg ccc tgt ctc acg ctg att ggc tct cct aat ttt ggg tac agg    1790
Ser Leu Pro Cys Leu Thr Leu Ile Gly Ser Pro Asn Phe Gly Tyr Arg
        480                 485                 490 tca gtt cac cgg gac ctg gag gcc cag att gcg atc gtg acg gag aac    1838
Ser Val His Arg Asp Leu Glu Ala Gln Ile Ala Ile Val Thr Glu Asn
    495                 500                 505 cag gcc ctg cag cag cag ctt cac cag gag caa gag cag ctc tac ctg    1886
Gln Ala Leu Gln Gln Gln Leu His Gln Glu Gln Glu Gln Leu Tyr Leu
510                 515                 520 agg tca ggt gtg gtg tcc tct gcc acc ttc gag cag ccg agt cgc cag    1934
Arg Ser Gly Val Val Ser Ser Ala Thr Phe Glu Gln Pro Ser Arg Gln
525                 530                 535                 540 gtg aag ctg tgg gtg aag atg gtg act cca ctg atc aag aac ttc ttc    1982
Val Lys Leu Trp Val Lys Met Val Thr Pro Leu Ile Lys Asn Phe Phe
            545                 550                 555 tga ggacagacag gtgctgtctc tagcatcacc tctcagcacg attttcccga         2035
 * gagttcacag gaatggcctt gatgaagatg acaggcatgg ccggggtcag ctctttcagc   2095
cgcgcttcag cgatgactcc agtctgggtg tcccagcgag cccctgcagg acagtatgg    2155 ctgagggtca ggtgtgctgc cagtaagtga gggaggggct ggcaggaagg gtggggtcct   2215
cacactcccc gccctytgca gagctgggct ctaccccaaa aggcttcagg ccagctgcca   2275
cagctggaag cagaggcctt cgtaggtgat ggcctgcatg ttgtaactac cccgtcccgc   2335
tgggctcaag gaacagctca gctaaagccc tcgggttcca tccgtttaaa tctgtggcat   2395
tttcagagcc tcatctgtca gccttaatgt cagtggcagg aagtcataac tccagctaaa   2455
aattacagag taaagttccc tgattcttaa tgtgtaatgt ctgccctatg tgtacataca   2515
caatataatt atacatctgt gcatataaat attgccttta accagactgc tattatttct   2575
actcgcccta tttaatggtg ttttatttc ctgtctgaaa tctcaaaata aacaaacatg    2635
gagagcttaa aaaaaaaaa aaagggcggc cgctagacta gtctagagaa a            2686

<210> SEQ ID NO 2
<211> LENGTH: 556
<212> TYPE: PRT
<213> ORGANISM: Homo sapiens
```

<400> SEQUENCE: 2

```
Met Ala Val Ala Ala Ala Ala Ala Gly Pro Val Phe Trp Arg Arg
  1               5                  10                  15

Leu Leu Gly Leu Leu Pro Gly Arg Pro Gly Leu Ala Ala Leu Leu Gly
             20                  25                  30

Arg Leu Ser Asp Arg Leu Gly Arg Asn Arg Asp Arg Gln Arg Arg
             35                  40                  45

Ser Pro Trp Leu Leu Leu Ala Pro Leu Leu Ser Pro Ala Val Pro Gln
         50                  55                  60

Val Thr Ser Pro Pro Cys Cys Leu Cys Pro Glu Gly Val His Arg Phe
 65                  70                  75                  80

Gln Trp Ile Arg Asn Leu Val Pro Glu Phe Gly Val Ser Ser His
                 85                  90                  95

Val Arg Val Leu Ser Ser Pro Ala Glu Phe Phe Glu Leu Met Lys Gly
                100                 105                 110

Gln Ile Arg Val Ala Lys Arg Val Val Met Ala Ser Leu Tyr Leu
                115                 120                 125

Gly Thr Gly Pro Leu Glu Gln Glu Leu Val Asp Cys Leu Glu Ser Thr
    130                 135                 140

Leu Glu Lys Ser Leu Gln Ala Lys Phe Pro Ser Asn Leu Lys Val Ser
145                 150                 155                 160

Ile Leu Leu Asp Phe Thr Arg Gly Ser Arg Gly Arg Lys Asn Ser Arg
                    165                 170                 175

Thr Met Leu Leu Pro Leu Leu Arg Arg Phe Pro Glu Gln Val Arg Val
                180                 185                 190

Ser Leu Phe His Thr Pro His Leu Arg Gly Leu Leu Arg Leu Leu Ile
                195                 200                 205

Pro Glu Arg Phe Asn Glu Thr Ile Gly Leu Gln His Ile Lys Val Tyr
    210                 215                 220

Leu Phe Asp Asn Ser Val Ile Leu Ser Gly Ala Asn Leu Ser Asp Ser
225                 230                 235                 240

Tyr Phe Thr Asn Arg Gln Asp Arg Tyr Val Phe Leu Gln Asp Cys Ala
                    245                 250                 255

Glu Ile Ala Asp Phe Phe Thr Glu Leu Val Asp Ala Val Gly Asp Val
                260                 265                 270

Ser Leu Gln Leu Gln Gly Asp Asp Thr Val Gln Val Val Asp Gly Met
                275                 280                 285

Val His Pro Tyr Lys Gly Asp Arg Ala Glu Tyr Cys Lys Ala Ala Asn
    290                 295                 300

Lys Arg Val Met Asp Val Ile Asn Ser Ala Arg Thr Arg Gln Gln Met
305                 310                 315                 320

Leu His Ala Gln Thr Phe His Ser Asn Ser Leu Leu Thr Gln Glu Asp
                    325                 330                 335

Ala Ala Ala Ala Gly Asp Arg Arg Pro Ala Asp Thr Trp Ile Tyr
                340                 345                 350

Pro Leu Ile Gln Met Lys Pro Phe Glu Ile Gln Ile Asp Glu Ile Val
                355                 360                 365

Thr Glu Thr Leu Leu Thr Glu Ala Glu Arg Gly Ala Lys Val Tyr Leu
    370                 375                 380

Thr Thr Gly Tyr Phe Asn Leu Thr Gln Ala Tyr Met Asp Leu Val Leu
385                 390                 395                 400

Gly Thr Arg Ala Glu Tyr Gln Ile Leu Leu Ala Ser Pro Glu Val Asn
                    405                 410                 415
```

```
Gly Phe Phe Gly Ala Lys Gly Val Ala Gly Ala Ile Pro Ala Ala Tyr
            420                 425                 430

Val His Ile Glu Arg Gln Phe Phe Ser Glu Val Cys Ser Leu Gly Gln
            435                 440                 445

Gln Glu Arg Val Gln Leu Gln Glu Tyr Trp Arg Arg Gly Trp Thr Phe
            450                 455                 460

His Ala Lys Gly Leu Trp Leu Tyr Leu Ala Gly Ser Ser Leu Pro Cys
465                 470                 475                 480

Leu Thr Leu Ile Gly Ser Pro Asn Phe Gly Tyr Arg Ser Val His Arg
                    485                 490                 495

Asp Leu Glu Ala Gln Ile Ala Ile Val Thr Glu Asn Gln Ala Leu Gln
            500                 505                 510

Gln Gln Leu His Gln Glu Gln Gln Leu Tyr Leu Arg Ser Gly Val
            515                 520                 525

Val Ser Ser Ala Thr Phe Glu Gln Pro Ser Arg Gln Val Lys Leu Trp
530                 535                 540

Val Lys Met Val Thr Pro Leu Ile Lys Asn Phe Phe
545                 550                 555

<210> SEQ ID NO 3
<211> LENGTH: 1671
<212> TYPE: DNA
<213> ORGANISM: Homo sapiens
<220> FEATURE:
<221> NAME/KEY: CDS
<222> LOCATION: (1)...(1671)

<400> SEQUENCE: 3 atg gcg gtg gcg gcg gca gct gcg gcg gga ccc gtg ttc tgg agg cga      48
Met Ala Val Ala Ala Ala Ala Ala Ala Gly Pro Val Phe Trp Arg Arg
  1               5                  10                  15 ctg ctg ggc ctc ctg cct ggc cgc cca ggg ctg gcc gcg ctc ctg gga      96
Leu Leu Gly Leu Leu Pro Gly Arg Pro Gly Leu Ala Ala Leu Leu Gly
                 20                  25                  30 cgc ctg tcc gac cgc ctc ggc agg aac cgg gac cgc cag cgc agg agg     144
Arg Leu Ser Asp Arg Leu Gly Arg Asn Arg Asp Arg Gln Arg Arg Arg
             35                  40                  45 tca cca tgg ctg tta ttg gct ccc ttg ctg tcc cca gct gtt ccc cag     192
Ser Pro Trp Leu Leu Leu Ala Pro Leu Leu Ser Pro Ala Val Pro Gln
         50                  55                  60 gtc acc tcc cca cct tgc tgc ctg tgt cca gaa ggc gtg cac cgg ttc     240
Val Thr Ser Pro Pro Cys Cys Leu Cys Pro Glu Gly Val His Arg Phe
 65                  70                  75                  80 cag tgg atc aga aac ctg gtt cca gaa ttt gga gtc tcc agt tct cac     288
Gln Trp Ile Arg Asn Leu Val Pro Glu Phe Gly Val Ser Ser Ser His
                 85                  90                  95 gtt agg gtg ctt tct tcc ccg gca gag ttt ttc gag ctc atg aag ggg     336
Val Arg Val Leu Ser Ser Pro Ala Glu Phe Phe Glu Leu Met Lys Gly
            100                 105                 110 cag ata aga gta gcc aag agg cgg gtc gtg atg gca tcc ctc tac ctg     384
Gln Ile Arg Val Ala Lys Arg Arg Val Val Met Ala Ser Leu Tyr Leu
        115                 120                 125 ggg aca ggt cct ttg gaa cag gag ctg gtg gac tgc ctg gaa agt act     432
Gly Thr Gly Pro Leu Glu Gln Glu Leu Val Asp Cys Leu Glu Ser Thr
    130                 135                 140 cta gaa aag tca ctc caa gca aag ttt cct tca aat ctc aag gtc tcc     480
Leu Glu Lys Ser Leu Gln Ala Lys Phe Pro Ser Asn Leu Lys Val Ser
145                 150                 155                 160
```

-continued

| | | |
|---|---|---|
| att ctc tta gac ttc acg cgg ggc tca cga ggt cgc aag aac tcc cgc<br>Ile Leu Leu Asp Phe Thr Arg Gly Ser Arg Gly Arg Lys Asn Ser Arg<br>                165                  170                  175 | | 528 |

```
att ctc tta gac ttc acg cgg ggc tca cga ggt cgc aag aac tcc cgc    528
Ile Leu Leu Asp Phe Thr Arg Gly Ser Arg Gly Arg Lys Asn Ser Arg
                165                 170                 175 aca atg ctg ctc cca ctc ctg cgg agg ttc cca gag cag gtc cga gtc    576
Thr Met Leu Leu Pro Leu Leu Arg Arg Phe Pro Glu Gln Val Arg Val
            180                 185                 190 tcc ctc ttt cac acg ccg cac ctc cgt ggg ctg ctt cgg ctc ctc atc    624
Ser Leu Phe His Thr Pro His Leu Arg Gly Leu Leu Arg Leu Leu Ile
        195                 200                 205 cct gag cgc ttc aac gag acc atc ggc ctc cag cac att aag gtg tac    672
Pro Glu Arg Phe Asn Glu Thr Ile Gly Leu Gln His Ile Lys Val Tyr
    210                 215                 220 ctc ttc gac aac agc gtc atc ttg agc ggt gca aac ctg agt gac tcc    720
Leu Phe Asp Asn Ser Val Ile Leu Ser Gly Ala Asn Leu Ser Asp Ser
225                 230                 235                 240 tac ttc acc aac cgc cag gac cgc tac gtg ttc ctg cag gac tgt gcg    768
Tyr Phe Thr Asn Arg Gln Asp Arg Tyr Val Phe Leu Gln Asp Cys Ala
                245                 250                 255 gag att gcc gac ttc ttc acg gag ctg gtg gac gcg gtg ggg gat gtg    816
Glu Ile Ala Asp Phe Phe Thr Glu Leu Val Asp Ala Val Gly Asp Val
            260                 265                 270 tcc ctg cag ctg cag ggg gac gac acg gtg cag gtg gtg gat ggg atg    864
Ser Leu Gln Leu Gln Gly Asp Asp Thr Val Gln Val Val Asp Gly Met
        275                 280                 285 gtg cat cct tac aaa ggg gac cgg gcc gag tac tgc aag gca gcc aat    912
Val His Pro Tyr Lys Gly Asp Arg Ala Glu Tyr Cys Lys Ala Ala Asn
    290                 295                 300 aag agg gtc atg gat gtg atc aac tca gcc agg acc cgc cag cag atg    960
Lys Arg Val Met Asp Val Ile Asn Ser Ala Arg Thr Arg Gln Gln Met
305                 310                 315                 320 ctg cat gcc cag acc ttc cac agc aac tct ctt ttg acc cag gaa gat   1008
Leu His Ala Gln Thr Phe His Ser Asn Ser Leu Leu Thr Gln Glu Asp
                325                 330                 335 gca gca gct gct ggg gat cgc aga cca gcc cct gac acc tgg att tat   1056
Ala Ala Ala Ala Gly Asp Arg Arg Pro Ala Pro Asp Thr Trp Ile Tyr
            340                 345                 350 ccg ctg att cag atg aag ccc ttc gag att caa atc gat gag att gtc   1104
Pro Leu Ile Gln Met Lys Pro Phe Glu Ile Gln Ile Asp Glu Ile Val
        355                 360                 365 act gag acc ctg ttg act gag gcg gag cgc ggg gca aag gtc tac ctc   1152
Thr Glu Thr Leu Leu Thr Glu Ala Glu Arg Gly Ala Lys Val Tyr Leu
    370                 375                 380 acc act ggc tat ttc aac ctg acc cag gcc tac atg gac ctg gtc ttg   1200
Thr Thr Gly Tyr Phe Asn Leu Thr Gln Ala Tyr Met Asp Leu Val Leu
385                 390                 395                 400 ggc act cgg gct gag tac cag atc ctg ctg gcc tca cca gag gtg aat   1248
Gly Thr Arg Ala Glu Tyr Gln Ile Leu Leu Ala Ser Pro Glu Val Asn
                405                 410                 415 ggc ttc ttt ggg gcc aag ggg gtg gcc ggc gcc atc cca gcg gcc tat   1296
Gly Phe Phe Gly Ala Lys Gly Val Ala Gly Ala Ile Pro Ala Ala Tyr
            420                 425                 430 gtg cac atc gag cga cag ttc ttc agt gag gtg tgc agc ctg gga cag   1344
Val His Ile Glu Arg Gln Phe Phe Ser Glu Val Cys Ser Leu Gly Gln
        435                 440                 445 cag gag cgg gtc cag ctt cag gag tac tgg cgg agg ggc tgg acg ttc   1392
Gln Glu Arg Val Gln Leu Gln Glu Tyr Trp Arg Arg Gly Trp Thr Phe
    450                 455                 460 cac gcc aaa ggc ctc tgg ctg tac ctg gca ggg agc agc ctg ccc tgt   1440
His Ala Lys Gly Leu Trp Leu Tyr Leu Ala Gly Ser Ser Leu Pro Cys
465                 470                 475                 480
```

```
ctc acg ctg att ggc tct cct aat ttt ggg tac agg tca gtt cac cgg         1488
Leu Thr Leu Ile Gly Ser Pro Asn Phe Gly Tyr Arg Ser Val His Arg
            485                 490                 495 gac ctg gag gcc cag att gcg atc gtg acg gag aac cag gcc ctg cag         1536
Asp Leu Glu Ala Gln Ile Ala Ile Val Thr Glu Asn Gln Ala Leu Gln
            500                 505                 510 cag cag ctt cac cag gag caa gag cag ctc tac ctg agg tca ggt gtg         1584
Gln Gln Leu His Gln Glu Gln Glu Gln Leu Tyr Leu Arg Ser Gly Val
            515                 520                 525 gtg tcc tct gcc acc ttc gag cag ccg agt cgc cag gtg aag ctg tgg         1632
Val Ser Ser Ala Thr Phe Glu Gln Pro Ser Arg Gln Val Lys Leu Trp
    530                 535                 540 gtg aag atg gtg act cca ctg atc aag aac ttc ttc tga                     1671
Val Lys Met Val Thr Pro Leu Ile Lys Asn Phe Phe *
545                 550                 555
```

The invention claimed is:

1. A method for identifying a compound which binds to an isolated polypeptide selected from the group consisting of:
   a) a polypeptide encoded by a nucleic acid molecule comprising a nucleotide sequence which is at least 95% identical to SEQ ID NO:1, SEQ ID NO:3, or the nucleotide sequence of the cDNA insert in the plasmid deposited with ATCC as Patent Deposit Number PTA-2011, wherein said polypeptide has phosphatidyl-glycerolphosphate synthase activity; and
   b) a polypeptide which is at least 95% identical to the amino acid sequence SEQ ID NO:2, wherein said polypeptide has phosphatidyl-glycerolphesphate synthase activity;

wherein said method comprises:
   i) contacting a test compound with said isolated polypeptide or a cell expressing said isolated polypeptide; and
   ii) determining whether said test compound binds to said polypeptide, thereby identifying a compound which binds to the polypeptide.

2. The method of claim 1, wherein said isolated polypeptide comprises the amino acid sequence of SEQ ID NO:2.

3. The method of claim 1, wherein the binding of said test compound to said isolated polypeptide is detected by a method selected from the group consisting of:
   a) detection of binding by direct detecting of test compound/polypeptide binding;
   b) detection of binding using a competition binding assay and;
   c) detection of binding using an assay for PGP synthase-mediated phospho-group transfer.

4. A method for identifying a compound which modulates the activity of an isolated polypeptide selected from the group consisting of:
   a) a polypeptide encoded by a nucleic acid molecule comprising a nucleotide sequence which is at least 95% identical to SEQ ID NO:1, SEQ ID NO:3, or the nucleotide sequence of the cDNA insert in the plasmid deposited with ATCC as Patent Deposit Number PTA-2011, wherein said polypeptide has phosphatidyl-glycerolphosphate synthase activity; and
   b) a polypeptide which is at least 95% identical to the amino acid sequence SEQ ID NO:2, wherein the polypeptide has phosphatidyl-glycerolphosphate synthase activity;

wherein said method comprises:
   i) contacting said isolated polypeptide with a test compound; and
   ii) determining the effect of said test compound on the activity of said isolated polypeptide wherein the determining comprises: a) incubating said polypeptide and its substrate in the presence and absence of the test compound; and b) determining the activity of said polypeptide in the presence and absence of the test compound, to thereby identify a compound that modulates the activity of said isolated polypeptide.

5. The method of claim 4, wherein the activity of said isolated polypeptide is increased in the reaction comprising the test compound compared to the activity in the absence of the test compound.

6. The method of claim 4, wherein the activity of said isolated polypeptide is decreased in the reaction comprising the test compound compared to the activity in the absence of the test compound.

7. The method of claim 4, wherein said isolated polypeptide comprises the amino acid sequence of SEQ ID NO:2.

8. The method of claim 7, wherein the activity of said isolated polypeptide is increased in the reaction comprising the test compound compared to the activity in the absence of the test compound.

9. The method of claim 7, wherein the activity of said isolated polypeptide is decreased in the reaction comprising the test compound compared to the activity in the absence of the test compound.

* * * * *